United States Patent
Ngu et al.

(10) Patent No.: US 7,432,271 B2
(45) Date of Patent: Oct. 7, 2008

(54) PYRAZOLYL INHIBITORS OF 15-LIPOXYGENASE

(75) Inventors: Khehyong Ngu, Pennington, NJ (US); David S. Weinstein, East Windsor, NJ (US); Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 523 days.

(21) Appl. No.: 10/932,981

(22) Filed: Sep. 1, 2004

(65) Prior Publication Data

US 2005/0070589 A1 Mar. 31, 2005

Related U.S. Application Data

(60) Provisional application No. 60/499,498, filed on Sep. 2, 2003.

(51) Int. Cl.
A61K 31/497 (2006.01)
C07D 241/10 (2006.01)
C07D 231/10 (2006.01)

(52) U.S. Cl. ............ 514/255.05; 544/224; 544/336; 548/356.1; 548/364.1; 514/252.1; 514/403; 514/406

(58) Field of Classification Search .......... 544/224, 544/336; 548/356.1, 364.1; 514/252.1, 255.05, 514/403, 406

See application file for complete search history.

(56) References Cited

OTHER PUBLICATIONS

U.S. Appl. No. 10/932,594, filed Sep. 1, 2004, Weinstein et al.
U.S. Appl. No. 10/932,457, filed Sep. 1, 2004, Weinstein.
Bleich, D., et al., "Resistance to type 1 diabetes induction in 12-lipoxygenase knockout mice", The Journal of Clinical Investigation, vol. 103, No. 10, pp. 1431-1436, May 1999.
Bocan, T., et al., "A specific 15-lipoxygenase inhibitor limits the progression and monocyte-macrophase enrichment of hypercholesterolemia-induced atherosclerosis in the rabbit", Atherosclerosis, vol. 136, pp. 203-216, 1998.
Kelavkar, U. et al., "The Effect of 15-Lipoxygenase-1 Expression on Cancer Cells", Current Urology Reports, vol. 3, pp. 207-214, 2002.
Setty, B.N., et al., 15-Hydroxyeicosatetraenoic Acid-Medicated Potentiation of Thrombia-Induced Platelet Functions Occurs Via Enhanced Production of Phosphoinositide-Derived Second Messengers—sn-1,2-Diacylglycerol and Inositol-1,4,5-Trisphosphate, Blood., vol. 80, No. 11, pp.
Sultana, S., et al., "Lipoxygenase Metabolites Induced Expression of Adhesion Molecules and Transendothelial Migration of Monocyte-Like HL-60 Cells Is Linked to Protein Kinase C Activation", Journal of Cellular Physiology, vol. 167, pp. 477-487, 1996.
Tisdale, M.J., "Protein Loss in Cancer Cachexia", Science's Compass, vol. 289, pp. 2293-2294. 2000.

*Primary Examiner*—Golam M Shameem
(74) *Attorney, Agent, or Firm*—Hong Liu; Maureen S. Gibbons

(57) ABSTRACT

The present invention provides pyrazolyl inhibitors of 15-LO, pharmaceutical compositions containing such inhibitors and methods for treating diseases related to the 15-LO cascade using such compounds and compositions.

4 Claims, No Drawings

PYRAZOLYL INHIBITORS OF 15-LIPOXYGENASE

RELATED APPLICATIONS

This application claims priority benefit under Title 35 § 119(e) of U.S. Provisional Application No. 60/499,498, filed Sep. 2, 2003, the contents of which are herein incorporated by reference.

FIELD OF THE INVENTION

The present invention relates to pyrazolyl inhibitors of the enzyme 15-lipoxygenase ("15-LO"), pharmaceutical compositions comprising said inhibitors, and methods of treating diseases responsive to inhibition of 15-lipoxygenase.

BACKGROUND OF THE INVENTION

The 15-LO cascade is implicated in various inflammatory disorders, including disorders involving the origin and recruitment of foam cells. Cholesterol is transported in blood particles called lipoproteins, which include low-density lipoproteins (LDL). Lipoproteins contain cholesterol and are necessary for foam cell formation. The formation of foam cells can lead to serious disorders. For example, hypercholesterolemia can induce monocytes to migrate into the arterial wall and mature into foam cells or tissue macrophages that accumulate fatty material, including cholesterol esters. Continued creation of foam cells thickens the inner lining of medium and large arteries, thereby forming atherosclerotic plaques or lesions containing cholesterol, smooth muscle cells, and connective tissue cells. Affected arteries lose elasticity and become narrowed or obstructed by the plaques indicating the onset of atherosclerosis. Atherosclerotic plaques may collect calcium, become brittle, and even rupture triggering the formation of a blood clot or thrombus capable of occluding an artery and causing a stroke or heart attack. In addition to atherosclerosis, hypercholesteremia plays a role in peripheral vascular diseases of small arteries, veins and lymphatics. Thus, hypercholesteremia may also affect the arms, legs, kidneys and other vital organs in addition to the heart and brain.

Lipoxygenases are enzymes that catalyze the oxidation of polyunsaturated fatty acids and esters thereof, including those found in low-density lipoproteins. In addition to metabolism of free fatty acids, the enzyme 15-lipoxygenase (15-LO) also oxidizes esterified polyenoic fatty acids. Related to its general pathology, it is believed that oxidative metabolites of the 15-LO cascade [e.g. the arachidonic acid metabolite 15-hydroperoxyeicosatetraenoic acid (15-HPETE)], induce endothelial cell activation and subsequent adhesion molecule expression resulting in monocyte recruitment to the vessel wall [Sultana et al, J. of Cellular Physiology 167 (1996) 467-487]. 15-Hydroxyeicosatetraenoic acid (15-HETE), a reduction product of 15-HPETE, has also been implicated in the potentiation of thrombin-induced platelet activation [Setty et al, Blood, 80:11 (1992): 2765-2773]. It has also been demonstrated that arachidonic acid metabolites of the 15-LO cascade, namely 15-hydroperoxyeicosatetraenoic acid (15-HPETE), induce a pro-thrombotic state in endothelial cells through enhancement of plasminogen activator inhibitor-1 (PAI-1) release. Additionally, evidence that 15-LO is involved in the pathology of diabetes, it has been demonstrated that deletion of the mouse gene homologue of 15-LO leads to a reduction of disease progression [Bleich et al, J Clin Invest (1999) May 15;103(10):1431-6]. 15-LO has also been implicated in the progression of various cancers [Kelavkar et al, Curr Urol Rep June 2002; 3(3):207-14]. Not only in the progression of the cancer itself, but also in its related pathologies including cachexia and wasting [Tisdale et al, Science 2000 Sep. 29;289(5488):2293-4].

Inhibition of 15-LO, therefore, would be useful to prevent and treat diseases with either an inflammatory component, a thrombotic component, or both as in the case of atherosclerosis, as well as various cancers. For example, it has been shown that treatment with a 15-LO inhibitor suppressed atherogenesis (or the production of atheroma—a fatty degeneration of the arterial wall) in rabbits fed a high-fat diet [Bocan et al, Atherosclerosis, 136 (1998): 203-216]. Additional diseases in which treatment with a 15-LO inhibitor would be useful include asthma, psoriasis, osteoarthritis, rheumatoid arthritis, Alzheimer's disease, and chronic obstructive pulmonary disease.

SUMMARY OF THE INVENTION

The present invention provides pyrazolyl inhibitors of 15-LO, pharmaceutical compositions containing such inhibitors, and methods for treating diseases related to the 15-LO cascade using such compounds and compositions. Specifically, the invention provides compounds of Formula I:

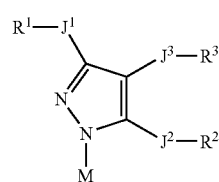

including enantiomers, diastereomers, salts and solvates thereof wherein:

$J^1$ is a bond, —C(O)—, —OC(O)—, —C(O)O—, —NR$^4$—, —NR$^4$—C(O)—, or —C(O)NR$^4$—;

$J^2$ is a bond, —C(O)—, —OC(O)—, —C(O)O—, —NR$^{4a}$—, —NR$^{4a}$—C(O)—, or —C(O)NR$^{4a}$—;

$J^3$ is alkylene, cycloalkylene, alkenylene or alkynylene each of which may be optionally substituted with $T^{1a}$, $T^{2a}$ and $T^{3a}$;

M is
  (1) hydrogen; or
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally substituted with $T^{1b}$, $T^{2b}$ and $T^{3b}$;

$R^1$ is
  (1) hydrogen; or
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally substituted with $T^{1c}$, $T^{2c}$ and $T^{3c}$;

$R^2$ is
  (1) hydrogen; or
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally substituted with $T^{1d}$, $T^{2d}$ and $T^{3d}$;

$R^3$ is —NR$^{3a}$SO$_2$Z, —NR$^{3a}$C(O)OZ, —NR$^{3a}$C(O)Z, —NR$^{3a}$C(O)NR$^{3b}$Z, or

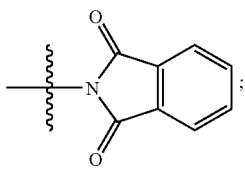

$R^{3a}$, $R^{3b}$, $R^4$ and $R^{4a}$ are each independently
  (1) hydrogen; or
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally independently substituted with $T^{1e}$, $T^{2e}$ and $T^{3e}$;

Z is
  (1) —$NR^5R^6$; or
  (2) alkyl, cycloalkyl, heterocyclo, aryl, heteroaryl, (cycloalkyl)alkyl, (heterocyclo)alkyl, (aryl)alkyl or (heteroaryl)alkyl, each of which may be optionally substituted with $T^{1f}$, $T^{2f}$ and $T^{3f}$;

$R^5$ and $R^6$ are independently
  (1) hydrogen;
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally independently substituted with $T^{1g}$, $T^{2g}$ and $T^{3g}$; or
  (3) —$C(O)R^7$, —$C(O)OR^7$, or —$OC(O)R^7$;

or $R^5$ and $R^6$ together with the nitrogen atom to which they are bonded can combine to form a 5 to 12-membered heterocyclo ring optionally substituted with $T^{1g}$, $T^{2g}$ and $T^{3g}$;

$R^7$ is
  (1) hydrogen; or
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally independently substituted with $T^{1h}$, $T^{2h}$ and $T^{3h}$;

$T^{1a-1h}$, $T^{2a-2h}$, and $T^{3a-3h}$ are optional substituents independently selected from
  (1) V, where V is
    (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
    (ii) a group (i) which is itself substituted by one or more of the same or different groups (i); or
    (iii) a group (i) or (ii) which is independently substituted by one or more (preferably 1 to 3) of the following groups (2) to (13) of the definition of T1,
  (2) —OH or —OV,
  (3) —SH or —SV,
  (4) —$C(O)_tH$, —$C(O)_tV$, or —O—C(O)V, where t is 1 or 2,
  (5) —$SO_3H$, —$S(O)_tV$, or $S(O)_tN(V^1)V$,
  (6) halo,
  (7) cyano,
  (8) nitro,
  (9) —$U^1$—$NV^2V^3$,
  (10) —$U^1$—$N(V^1)$—$U^2$—$NV^2V^3$,
  (11) —$U^1$—$N(V^4)$—$U^2$—V,
  (12) —$U^1$—$N(V^4)$—$U^2$—H,
  (13) oxo;

$U^1$ and $U^2$ are each independently
  (1) a single bond,
  (2) —$U^3$—$S(O)_t$—$U^4$—,
  (3) —$U^3$—C(O)—$U^4$—,
  (4) —$U^3$—C(S)—$U^4$—,
  (5) —$U^3$—O—$U^4$—,
  (6) —$U^3$—S—$U^4$—,
  (7) —$U^3$—O—C(O)—$U^4$—,
  (8) —$U^3$—C(O)—O—$U^4$—,
  (9) —$U^3$—C(=$NV^{1a}$)—$U^4$—, or
  (10) —$U^3$—C(O)—C(O)—$U^4$—;

$V^1$, $V^{1a}$, $V^2$, $V^3$ and $V^4$
  (1) are each independently hydrogen or a group provided in the definition of $T^1$; or
  (2) $V^2$ and $V^3$ may together be alkylene or alkenylene, completing a 3- to 8-membered saturated or unsaturated ring together with the atoms to which they are attached, which ring is unsubstituted or substituted with one or more groups listed in the definition of $T^1$, or
  (3) $V^2$ or $V^3$, together with $V^1$, may be alkylene or alkenylene completing a 3-to 8-membered saturated or unsaturated ring together with the nitrogen atoms to which they are attached, which ring is unsubstituted or substituted with one or more groups listed in the definition of $T^1$, or
  (4) $V^2$ and $V^3$ together with the nitrogen atom to which they are attached may combine to form a group —N=$CV^5V^6$ where $V^5$ and $V^6$ are each independently H or a group provided in the definition of V; and $U^3$ and $U^4$ are each independently
  (1) a single bond,
  (2) alkylene,
  (3) alkenylene, or
  (4) alkynylene;

provided that
  (1) groups -$J^1$-$R^1$ and -$J^2$-$R^2$ are not both hydrogen; and
  (2) when $J^1$ is —$NR^4$—,
    (a) neither $R^1$ or $R^4$ are a cephalosporin group of formula

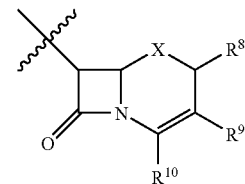

wherein
  X is O, S, $NR^{11}$, or $CH_2$;
  $R^8$ is hydrogen or alkyl
  $R^9$ is alkyl optionally substituted with —$OC(O)CH_3$ or —S-(tetrazolyl) wherein the tetrazole ring is optionally subtituted with alkyl;
  $R^{10}$ is COOH;
  $R^{11}$ is hydrogen, alkyl, formyl, or benzyl; and
  (b) $R^1$ and $R^4$ are not both hydrogen when -$J^2$-$R^2$ is hydrogen.

Preferred compounds within the scope of formula I include compounds wherein:
  $J^1$ is a bond;
  $J^2$ is a bond;
  $J^3$ is alkylene or cycloalkylene either of which may be optionally substituted with $T^{1a}$, $T^{2a}$ and $T^{3a}$;
  M is hydrogen;
  $R^1$ is alkyl, aryl or heteroaryl any of which may be optionally substituted with $T^{1c}$, $T^{2c}$ and $T^{3c}$;
  $R^2$ is aryl or heteroaryl either of which may be optionally substituted with $T^{1d}$, $T^{2d}$ and $T^{3d}$;
  $R^3$ is —$NR^{3a}SO_2Z$;
  $R^{3a}$ is H or alkyl;

Z is —NR$^5$R$^6$, or aryl optionally substituted with T$^{1f}$, T$^{2f}$ and T$^{3f}$;

R$^5$ is
  (1) hydrogen; or
  (2) alkyl or (aryl)alkyl either of which may be optionally substituted with T$^{1g}$, T$^{2g}$ and T$^{3g}$;

R$^6$ is
  (1) hydrogen; or
  (2) alkyl, aryl, heteroaryl, heterocyclo, (aryl)alkyl, (heteroaryl)alkyl, or (heterocylo)alkyl, any of which may be optionally substituted with T$^{1g}$, T$^{2g}$ and T$^{3g}$;
  (3) —C(O)OR$^7$;

or R$^5$ and R$^6$ together with the nitrogen atom to which they are bonded combine to form a 5 to 10-membered heterocyclo ring (such as piperazine, piperadine, morpholine, pyrolidine, pyrazoldine, oxazolidine, 1,4-dioxa-8-aza-spiro[4.5] decane, or 1,3,8-Triaza-spiro[4.5]decane) which may be optionally substituted with T$^{1g}$, T$^{2g}$ and T$^{3g}$; and R$^7$ is alkyl, aryl, (aryl)alkyl, any of which may be optionally substituted with T$^{1h}$, T$^{2h}$ and T$^{3h}$.

More preferred compounds within the scope of formula I include compounds wherein:

J$^1$ is a bond;
J$^2$ is a bond;
J$^3$ is alkylene (especially ethylene or n-propylene) or cycloalkylene (especially cyclopropylene);
M is hydrogen;
R$^1$ is aryl (especially phenyl) or heteroaryl (especially thiazole, pryidine, pyrimidine, or thiophene) either of which may be optionally substituted with T$^{1c}$, T$^{2c}$ and T$^{3c}$ (especially where T$^{1c}$, T$^{2c}$ and T$^{3c}$ are independently selected from alkyl, —OV (especially where V is alkyl), halo, and nitro);
R$^2$ is aryl (especially phenyl) or heteroaryl (especially benzofuran, or pyridine) either of which may be optionally substituted with T$^{1d}$, T$^{2d}$ and T$^{3d}$ (especially where T$^{1d}$, T$^{2d}$ and T$^{3d}$ are independently selected from alkyl, haloalkyl, halo, —OV (especially where V is alkyl), and —S(O)$_t$V (especially where V is alkyl));
R$^3$ is —NR$^{3a}$SO$_2$Z;
R$^{3a}$ is H;
Z is —NR$^5$R$^6$, or phenyl optionally substituted with T$^{1d}$, T$^{2d}$ and T$^{3d}$ (especially where T$^{1d}$, T$^{2d}$ and T$^{3d}$ are independently selected from alkyl, halo, —C(O),H, —C(O)$_t$V (especially where V is alkyl), —U$^1$—N(V$^4$)—U$^2$—V (especially where U$^1$ is a bond, U$^2$ is —C(O)—, V$^4$ is H or alkyl, and V is alkyl), (hydroxy)alkyl, alkyl substituted with —U$^1$—NV$^2$V$^3$ (especially where U$^1$ is a bond, V$^2$ is hydrogen or alkyl and V$^3$ is alkyl optionally substituted with a group —U$^{1*}$—NV$^{2*}$V$^{3*}$ where U$^{1*}$ is a bond, V$^{2*}$ is hydrogen or alkyl, V$^{3*}$ is hydrogen or alkyl, or V$^{2*}$ and V$^{3*}$ combine to form a heterocyclo ring such as pyrolidine, priperadine, piperazine, or morpholine);
R$^5$ is hydrogen, or alkyl optionally substituted with T$^{1g}$ (especially where T$^{1g}$ is —U$^1$—NV$^2$V$^3$ (especially where U$^1$ is a bond, and V$^2$ and V$^3$ are independently hydrogen, alkyl, aryl or (aryl)alkyl));
R$^6$ is
  (1) alkyl optionally substituted with T$^{1g}$, T$^{2g}$ and T$^{3g}$ (especially where T$^{1g}$, T$^{2g}$ and T$^{3g}$ are independently selected from —U$^1$—NV$^2$V$^3$ (especially where U$^1$ is a bond, and V$^2$ and V$^3$ are independently hydrogen, alkyl, aryl or (aryl)alkyl wherein said aryl groups are optionally substituted with alkyl),
  (2) aryl, heteroaryl, (aryl)alkyl, or (heteroaryl)alkyl, any of which may be optionally substituted with T$^{1g}$, T$^{2g}$ and T$^{3g}$ (especially where T$^{1g}$, T$^{2g}$ and T$^{3g}$ are independently selected from alkyl, —OV (especially where V is alkyl), haloalkyl, halo, —U$^1$—NV$^2$V$^3$ (especially where U$^1$ is a bond, and V$^2$ and V$^3$ are independently hydrogen, alkyl, aryl or (aryl)alkyl wherein said aryl groups are optionally substituted with alkyl), heterocyclo, or (aryl)alkenyl where the aryl group is optionally substituted with —U$^1$—NV$^2$V$^3$);
  (3) heterocyclo or (heterocylo)alkyl, either of which may be optionally substituted with T$^{1g}$, T$^{2g}$ and T$^{3g}$ (especially where T$^{1g}$, T$^{2g}$ and T$^{3g}$ are independently selected from, alkyl, —C(O),H, —C(O)$_t$V (especially where V is alkyl), (aryl)alkyl wherein the aryl group is optionally substituted with one or more haologen, haloalkyl, or alkynyl); or
  (4) —C(O)OR$^7$;

or R$^5$ and R$^6$ together with the nitrogen atom to which they are bonded combine to form piperazine, piperadine, morpholine, pyrolidine, pyrazoldine, oxazolidine, 1,4-dioxa-8-aza-spiro[4.5]decane, or 1,3,8-Triaza-spiro[4.5]decane any of which may be optionally substituted with T$^{1g}$, T$^{2g}$ and T$^{3g}$ (especially where T$^{1g}$, T$^{2g}$ and T$^{3g}$ are independently selected from alkyl (optionally substituted with alkoxy, or hydroxy), (heterocyclo)alkyl, aryl (optionally substituted with one or more alkoxy, halo, alkyl, haloalkyl, or nitro), (aryl)alkyl (wherein the aryl group is optionally further substituted with one or more alkoxy, halo, alkyl, haloalkyl, or nitro), —C(O)$_t$H, —C(O)$_t$V (especially where V is alkyl), alkenyl, (aryl)alkenyl, cycloalkyl, heteroaryl (optionally substituted with cyano, alkyl, or haloalkyl), oxo, hydroxy, alkoxy, heterocyclo, or nitro ); and R$^7$ is alkyl, aryl, or (aryl)alkyl, wherein said aryl groups are optionally further substituted with one or more alkyl groups.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are often most preferred.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

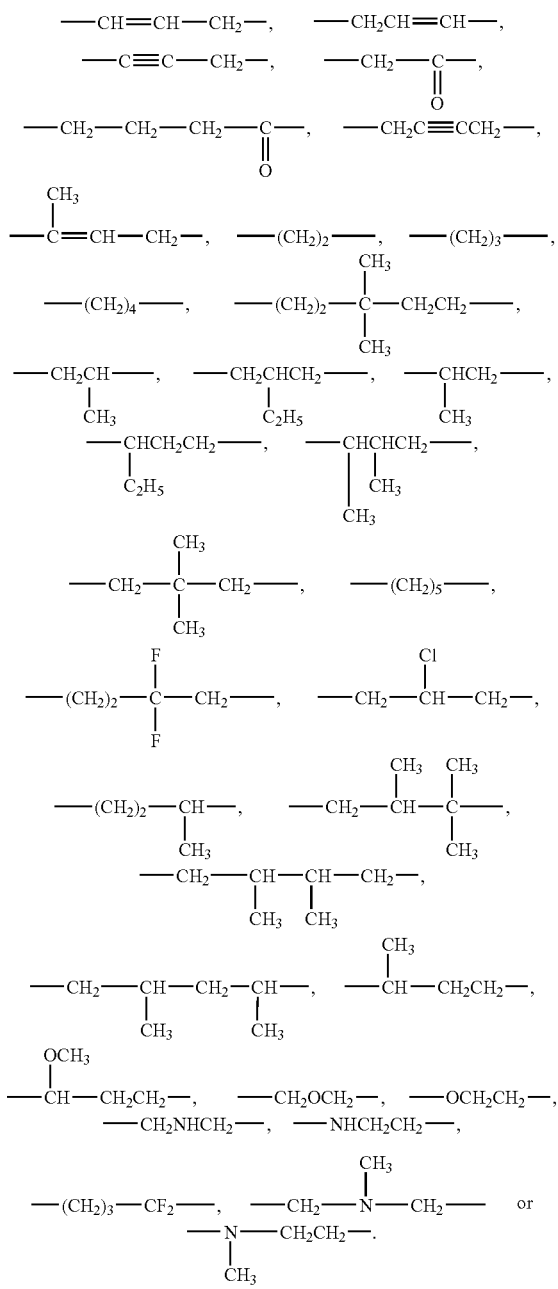

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The rings of multi-ring cycloalkyls may be either fused, bridged and/or joined through one or more spiro union to 1 or 2 aromatic cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

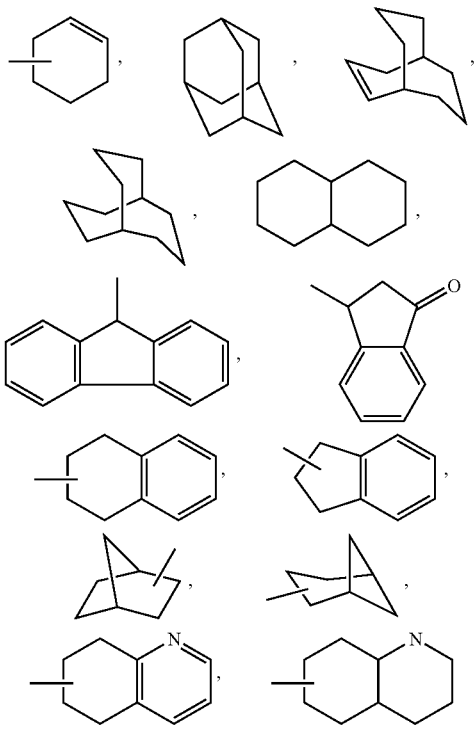

and the like.

The term "cycloalkylene" as employed herein refers to a "cycloalkyl" group which includes free bonds and thus is a linking group such as

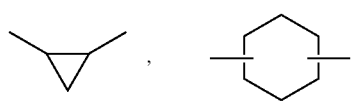

and the like.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

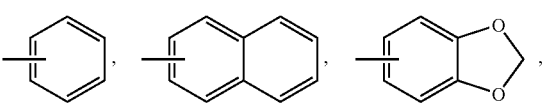

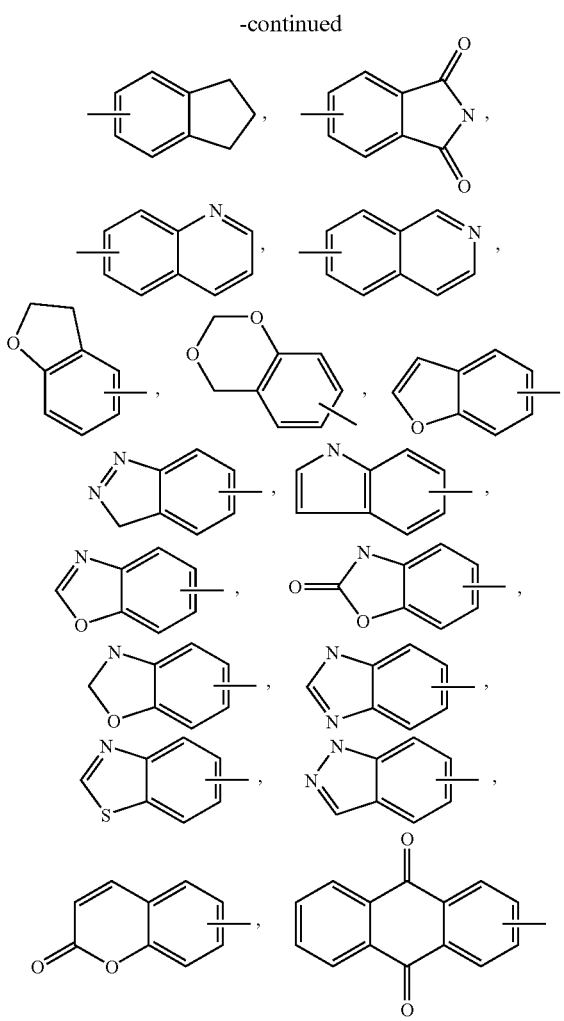

and the like.

The terms "halogen" and "halo" as used herein by itself or as part of another group refer to fluorine, chlorine, bromine and iodine. Haloalkyl refers to an alkyl chain substituted with from one to three halogens.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaterized. Examples of heteroaryl groups include the following:

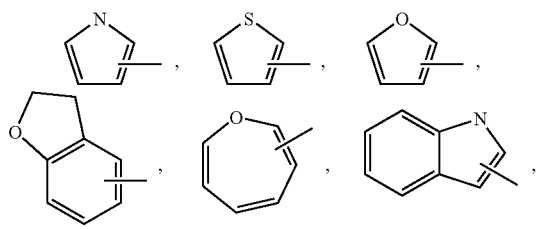

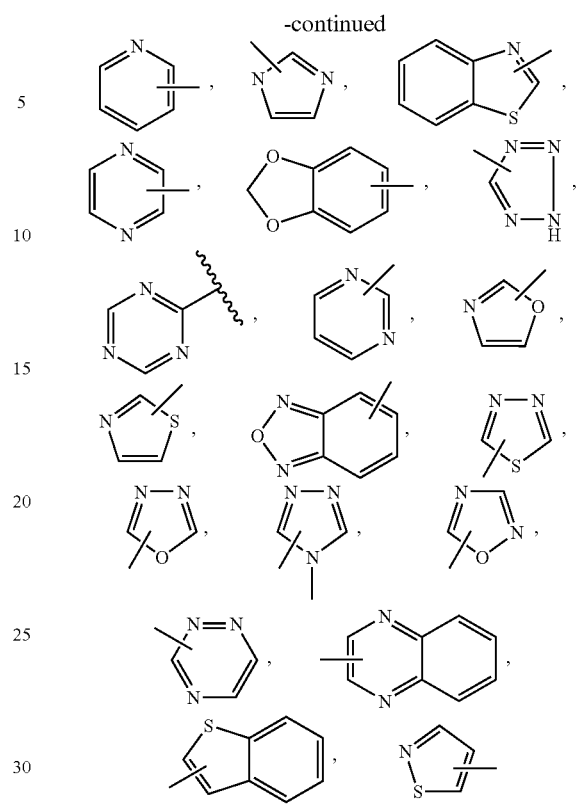

and the like.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl , oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

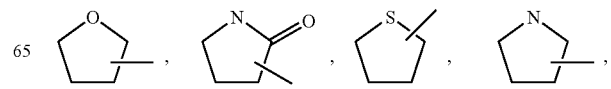

-continued

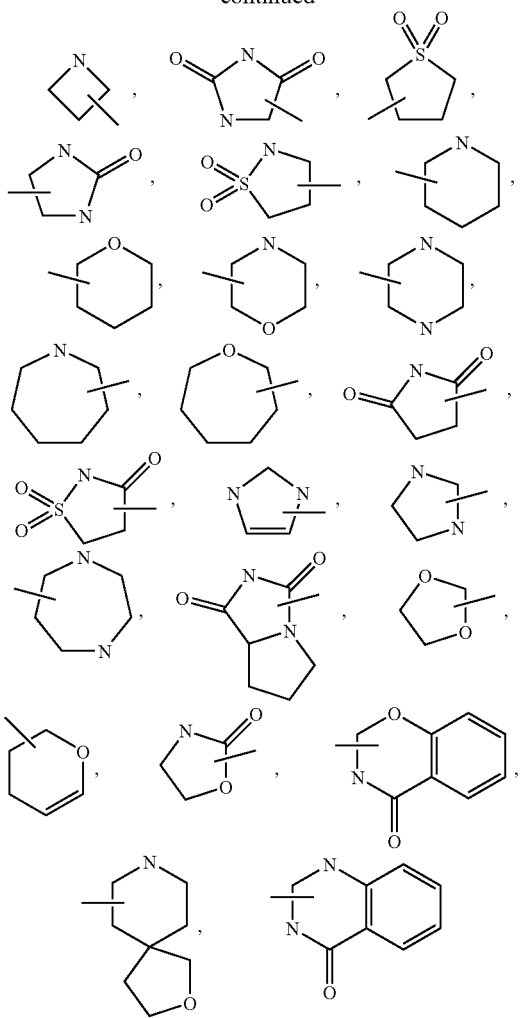

and the like.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl), and each of which (homocyclic or heterocyclic) may optionally be substituted by one or more (such as one to three) hydrogen, halogen, cyano, alkyl, alkoxy, nitro or trifluoromethyl groups.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates. Any tautomers which may exist are also contemplated herein as part of the present invention.

All stereoisomers of the present compounds, such as those which may exist due to asymmetric carbons on the R substituents, including enantiomeric forms (which may exist even in the absence of asymmetric carbons, e.g., atropisomers) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Methods of Preparation

The compounds of the present invention may be prepared by methods such as those illustrated in Scheme 1. Solvents, temperatures, pressures, and other reaction conditions may be selected by one of ordinary skill in the art. Starting materials are commercially available or readily prepared by one of ordinary skill in the art.

Scheme 1 illustrates the synthesis of pyrazoles via intermediate 1,3-dicarbonyl compounds. Gamma-chloro ketones II not available from commercial vendors may be prepared by the method of Sato et al. (Chem. Pharm. Bull., 1978, 3296-3305). Alternatively, gamma-chloro aryl propyl ketones may be prepared from Weinreb amide I (Shimizu et al. Tetrahedron Letters.; EN; 38; 15; 1997; 2685-2688) by treatment with an organometallic nucleophile (organolithium, Grignard reagentor the like) at low temperature (typically −78° C.) to give an intermediate chloroketone II. The chloride may then be displaced by azide anion (sodium azide or a related salt) between 0-100° C. (typically 70° C.) to give the azide product III ($X=N_3$). Alternatively, the phthalimide product III (X=NPhth) may be prepared from chloroketone II by displacement of chloride with phthalimide anion (typically potassium phthalimide). Treament of ketone III with a suitable base (e.g., lithium bis(trimethylsilyl)amide or lithium diisopropylamide) at low temperature (typically −78° C.) will provide an enolate intermediate which may then react with a suitably activated carboxylic acid derivative (acid chloride, Weinreb amide, N-hydroxy succinimide ester or the like) to provide a 1,3-dicarbonyl intermediate IV. Condensation of the 1,3-dicarbonyl compound IV with a hydrazine gives a pyrazole product which may be formed either as isomer Va, Vb, or a mixture of both. Isomers Va and Vb may typically be separated by flash column chromatography or preparative HPLC. Reduction of Va or Vb when X=azide ($N_3$) to provide amine VIa or VIb may be carried out under heterogeneous catalytic hydrogenation conditions, typically using palladium on carbon (10% w/w) and hydrogen gas in methanol as solvent. Alternatively, reduction of the azide may be accomplished by Staudinger reduction (triphenylphosphine, water). When X=phthalimide, treatment of Va or Vb with hydrazine in methanol or a mixture of THF and methanol at 0-100° C. (typically 70° C.) provides the amine VIa or VIb.

Further elaboration of the amine to the final compounds may be accomplished using ordinary techniques known to one skilled in the art. Non-symmetrical sulfamides have been prepared via intermediate N-sulfamoyloxazolidinones following the method of Ducry et al. (Helv. Chim. Act. 1992, 82 (12), 2432-2447). Typically, to 1 eq. of chlorosulfonyl isocyanate in dry dichloromethane (0.22 M) at −20° C. is added 2-chloroethanol dropwise. The temperature is allowed to warm to 0° C. and the solution maintained at that temperature for 1.5 h. The solution is then cooled to −20° C. and added via canula to a solution (or suspension) of an amine (1 eq.) and triethylamine (7 eq) in dichloromethane (0.25 M) at 0° C. The reaction mixture is allowed to warm to and maintained at room temperature 16 h. The intermediate sulfamoyloxazolidinone may be purified by preparative HPLC. Alternatively, the reaction mixture may be concentrated in vacuo and used directly in the next step without further purification.

Heating a solution of the intermediate sulfamoyloxazolidinone in dry acetonitrile (0.1-0.5 M) in the presence of excess triethylamine (7-10 eq) at 70° C. for 17 h, followed by purification by preparative HPLC provides the sulfamides.

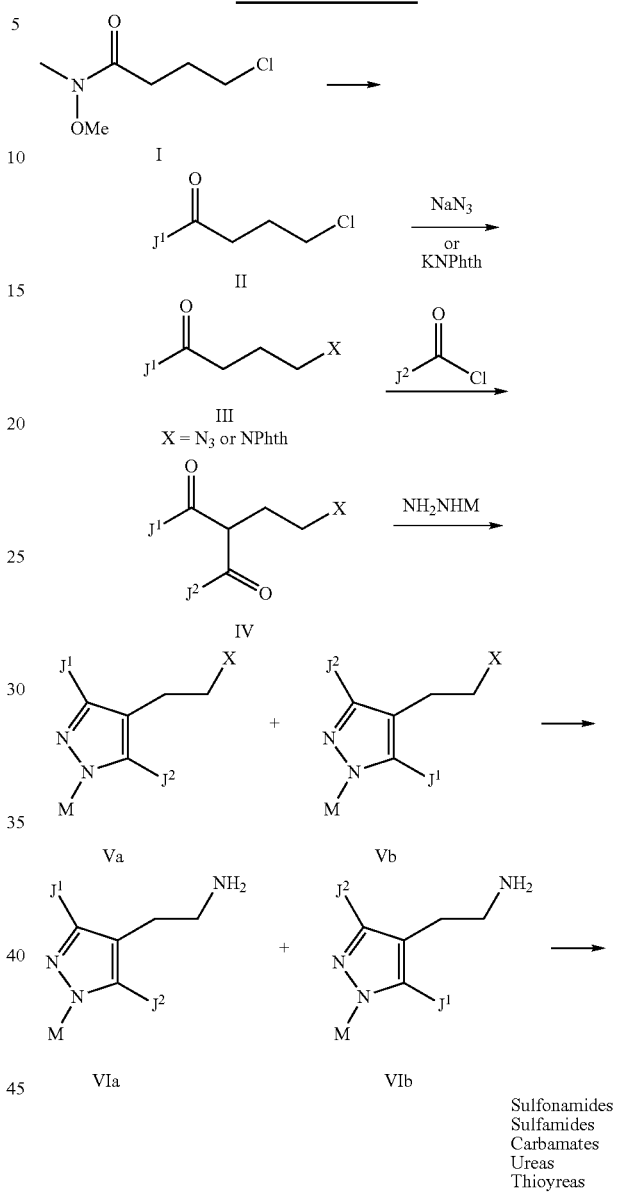

SCHEME 1
Synthesis of Pyrazoles

Sulfonamides
Sulfamides
Carbamates
Ureas
Thioyreas

Utility and Combinations

The compounds of formula I and salts thereof are inhibitors of 15-LO and are useful in treatment of various inflammatory disorders, including disorders involving the origin and recruitment of foam cells. The compounds of the present invention may be employed alone or in combination with each other and/or other suitable therapeutic agents useful in the treatment of 15-LO mediated disorders such as atherosclerosis, treating or preventing inflammation; diabetes; vascular restenosis; hypertension; asthma; rheumatiod arthritis; osteoarthritis; cancer; and inflammatory bowel disease.

Additionally, the compounds are useful in treating or preventing symptoms or consequences occurring from thrombosis and/or the formation of atherosclerotic plaques, atherosclerosis, peripheral arterial disease, coagulation syndromes, and intermittent claudication. The compounds may be used to treat thrombotic or thromboembolic conditions such as thromboembolic stroke (including that resulting from atrial fibrillation or from ventricular mural thrombus); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequenses of medication (such as oral contraceptives, hormome replacement and heparin); thrombotic consequenses of atherosclerotic vascular disease and atherosclerotic plaque rupture leading to tissue ischemia; prevention of atherosclerotic plaque formation; transplant atherosclerosis; thromboembolic complications of pregancy including fetal loss; thromboembolic consequenses of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation); coagulation syndromes; vascular remodeling atherosclerosis, restenosis and systemic infection; prevention of metastasis and tumor implantation; diabetic complications including retinopathy, nephropathy and neuropathy; inflammation; Kasabach-Merritt syndrome; atrial fibrillation; ventricular enlargement (including dilated cardiac myopathy and heart failure); restenosis (e.g., following arterial injury-induced either endogenously or exogenously).

In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation. Additionally, the compounds may be used for preservation of tissue as related to organ transplantation.

The inventive compounds also are useful in treating diseases or disorders in other tissues or muscles that are associated with inflammatory conditions. For example, the compounds may be used to treat muscle cell damage and necrosis.

Additionally, the inventive compounds may be useful as anti-cancer and/or anti-tumor agents.

The present invention thus provides methods for the treatment of these disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to endothelin-dependent or angiotensin II-dependent disorders.

The present invention also provides pharmaceutical compositions comprising at least one of the compounds of the formula I capable of treating a 15-LO mediated disorder in an amount effective therefor, and a pharmaceutically acceptable vehicle, carrier or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat peripheral vascular diseases and as such may be formulated as a cream or ointment.

The compounds of the present invention may also be employed in combination with other suitable therapeutic agents that a patient suffering from a 15-LO mediated disorder might also likely be taking other therapeutic agents such as potassium channel openers, calcium channel blockers, sodium hydrogen exchanger inhibitors, anti-arrhythmic agents, thrombin inhibitors, platelet aggregation inhibitors or anti-platelet agents, fibrinogen antagonists, diuretics, anti-hypertensive agents, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-oxidant agents; angiogenesis modulators; anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

For example, the inventive compounds may be used in combination with aspirin, clopidogrel, ticlopidine or CS-747, warfarin, and low molecular weight heparins (such as lovenox, enoxaparain, and dalteparin). Other suitable therapeutic agents in combination with which the inventive compounds may be used include:

anti-arrhythmic agents including Class I agents (such as propafenone); Class II agents (such as carvedilol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in U.S. application Ser. No. 09/729,731, filed Dec. 5, 2000;

alpha- or beta-adrenergic blockers (such as propranolol, nadolol and carvedilol), or -β-adrenergic agonists such as albuterol, terbutaline, formoterol, salmeterol, bitolterol, pilbuterol, and/or fenoterol;

angiotensin-II receptor antagonists (e.g., irbesartan, losartan or valsartan);

anticholinergics such as ipratropium bromide;

anti-diabetic agents such as biguanides (e.g. motormen); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors.

anti-depressant or anti-anxiety agents such as nefazodone, sertraline, diazepam, lorazepam, bastioned, and hydrolyzing palmate;

anti-diabetic agents such as biguanides (e.g. motormen); glucosidase inhibitors (e.g. acarbose); insulins (including insulin secretagogues or insulin sensitizers); meglitinides (e.g. repaginate); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual, agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors anti-hypertensive agents such as angiogenesis-converting enzyme (ACE) inhibitors (e.g., caporal, lisinopril, zofenopril, armorial, fosinopril, enalapril, ceranopril, cilazopril, delapril, pectoral, quinapril), vasopeptidase inhibitors, i.e., dual ACE/NEP inhibitors (e.g., omapatrilat and gemopatrilat), AT-1 receptor antagonists (e.g., losartan, irbesartan, valsartan); ET receptor antagonists (e.g., sitaxsentan, arsenate and compounds disclosed in U.S. Pat. Nos. 5,612,359 and 6,043,265); Dual ET/AII antagonist (e.g., compounds disclosed in WO 00/01389); neutral end peptidase (NEP) inhibitors;

anti-inflammatory agents such as cromolyn, nedocromil, theophylline, zileuton, zafirlukast, monteleukast and/or pranleukast or corticosteroids including beclomethasone, triamcinolone, budesonide, fluticasone, flunisolide or dexamethasone; prednisone; dexamethasone; enbrel; protien tyrosine kinase (PTK) inhibitors; cyclooxygenase inhibitors (including NSAIDs, and COX-1 and/or COX-2 inhibitors); aspirin; or indomethacin; other lipoxygenase inhibitors; chemokine receptor modulators (including CCR1, CCR2, CCR3, CXCR2 receptor antagonists); secretary and cryptozoic phospholipase A2 inhibitors; VLA4 antagonists; cytokine modulators (e.g. TNF-alpha converting enzyme (TACE) inhibitors, Interleukin-1 converting enzyme (ICE) inhibitors, Interleukin-1 receptor antagonists);

angiogenesis modulators such as understating;

anti-oxidant agents and/or lipid per oxidation inhibitors such as produce, BO-653, Vitamin A, Vitamin E, AGI-1067;

anti-platelet agents such as GPIIb/GPIIIa blockers, (e.g., abciximab, eptifibatide, tirofiban); $P2Y_{12}$ antagonists (e.g., clopidogrel, ticlopidine, CS-747); or thromboxane receptor antagonists (e.g., ifetroban);

anti-osteoporosis agents including alendronate and raloxifene.

anti-obesity agents including orbital and aP2 inhibitors (such as those disclosed in U.S. Ser. No. 09/519,079 filed Mar. 6, 2000);

anti-proliferative agents for use in combination with the compounds of the present invention include cyclosporine A, palliate, FK 506, and adriamycin;

anti-ulcer and gastro esophageal reflux disease agents including famotidine, ranitidine, and omeprazole;

sodium hydrogen exchanger-1(NHE-1) inhibitors such as caryopsides;

calcium channel blocking agents such as verapamil, nifedipine, diltiazem, amlodipine and mybefradil;

cardiac glycosides such as digitalis and outbid;

diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride;

hormone replacement therapies including estrogen (e.g., conjugated estrogens) and estradiol;

lipid profile modulators including HMG-CoA reeducates inhibitors (e.g., pravastatin, impastation, atorvastatin, fluvastatin, cerivastatin, AZ4522, itavastatin [Nissan/Kowa]), ZD-4522 (a.k.a. rosuvastatin, or atavastatin or visitation)); squalene synthesize inhibitors; fibrates; bile acid sequestrants (such as quest ran); ACAT1 inhibitors; ACAT2 inhibitors; dual ACAT½ inhibitors; MTP inhibitors; cholesterol absorption inhibitors such as Eztemibe; and cholesterol ester transfer protein inhibitors (e.g., CP-529414); PPAR-delta agonists; PPAR-alpha agonists; dual PPAR-alpha/delta agonists; LXR-alpha agonists; LXR-beta agonists; LXR dual alpha/beta agonists;

mineral corticoid receptor antagonists such as spironolactone and eplirinone.

microtonal triglyceride transport protein inhibitors (such as disclosed in U.S. Pat. Nos. 5,739,135, 5,712,279 and 5,760,246);

phosphodiesterase (PDE) inhibitors including dipyridamole, cilostazol, or sildenafil, or PDE inhibitors in combination with aspirin, ifetroban, picot amide, ketanserin, clopidogrel, and/or thromboxane receptor antagonists or thromboxane A synthesize inhibitors (such as picot amide);

serotonin-2-receptor antagonists (such as ketanserin), fibrinogen receptor antagonists, and thrombolytic agents, such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), factor VIIa inhibitors, factor Xa inhibitors, thrombin inhibitors (such as heroin and argatroban), animal salivary gland plasminogen activators, PAI-1 inhibitors such as XR-330 and T-686, and inhibitors of α-2-antiplasmin such as anti-α-2-antiplasmin antibody, prostacyclin mimetics.

The inventive compounds may also be useful in combination with other anticancer strategies and chemotherapies such as taxi and/or capsulation. The compounds may be used in conjunction with anti-tumor agents such as palliate, adriamycin, epithilones, cisplatin, and carboplatin.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to allow for increased efficacy and/or reduced doses of any of the above agents and therefore minimize potential hemorrhagic side-effects.

If formulated as a fixed dose, such combination products employ the compounds of this invention within the dosage range described and the other pharmaceutically active agent within its effective dosage range. The above other therapeutic agents, when employed in combination with the compounds of the present invention, may be used, for example, in those amounts indicated in the Physicians' Desk Reference (PDR) or as otherwise determined by one of ordinary skill in the art.

The following assays may be employed in ascertaining the degree of activity of a compound as a 15-LO inhibitor. Compounds described in the following Examples have demonstrated measurable activity as 15-LO inhibitors. The inhibitory activity of the Examples against purified 15-LO enzyme was determined using a standard colorimetric assay in which the lipid hydroperoxide product of either linoleic or arachidonic acid [13-hydroperoxyoctadecadienoic acid (13-HPODE) and 15-hydroperoxyeicosatetraenoic acid (15-HPETE), respectively] oxidizes $Fe2+$ under mildly acidic conditions [Jiang et al, Lipids (1991), 26:10, 853-856]. The $Fe3+$ forms a chromospheres with xylenol orange that absorbs strongly at 560 nm. Inhibitory activity was compared to an uninhibited (maximal) reaction to yield % inhibition (compound concentration in which enzyme activity is reduced by 50% is termed the $IC_{50}$). 15-LO enzyme was obtained from phenylhydrazine-treated rabbits and purified according to the method of Rapoport et al [European Journal of Biochemistry (1979) 96:545-561]. In addition to the colorimetric assay, a standard spectrophotometric kinetic assay [Gan et al, *J. Biological Chemistry* (1996), 271:41; 25412-2541877] was also employed to measure compound activity as 15-LO inhibitors. This assay determines enzyme activity by monitoring the increased absorbance at 234 nm that results from conjugated diene formation of the metabolized substrate. Reactions were carried out 3 minutes and the linear part of the curve was utilized to calculate reaction rates. IC50 calculations were as described for the colorimetric assay.

EXAMPLES

The following Examples illustrate embodiments of the present invention, and are not intended to limit the scope of the claims. Compounds of the Examples are identified by the example and step in which they are prepared (for example, "1A" denotes the title compound of step A of Example 1), or by the example only where the compound is the title compound of the example (for example, "4" denotes the title compound of Example 4).

General Procedure: Purification by Reverse-Phase Preparative HPLC

Reverse-phase preparative HPLC was performed with Shimadzu 8A liquid chromatographs using YMC S5 ODS columns (20×100, 20×250, or 30×250 mm). Gradient elution was performed with methanol/water mixtures in the presence of 0.1% TFA.

Analytical HPLC Methods Employed in Characterization of Examples

Analytical HPLC was performed on Shimadzu LC10AS liquid chromatographs using either of the following methods:

Method A:
  Linear gradient of 0 to 100% solvent B over 4 min, with 1 min hold at 100% B.
  UV visualization at 220 nm
  Column: YMC S5 ODS Ballistic 4.6×50 mm
  Flow rate: 4 ml/min
  Solvent A: 0.2% phosphoric acid, 90% water, 10% methanol
  Solvent B: 0.2% phosphoric acid, 90% methanol, 10% water Method B:
  Linear gradient of 0 to 100% solvent B over 2 min, with 1 min hold at 100% B.
  UV visualization at 220 nm
  Column: Phenomenex 4.6×30 mm
  Flow rate: 5 ml/min
  Solvent A: 0.1% trifluoroacetic acid, 90% water, 10% methanol
  Solvent B: 0.1% trifluoroacetic acid, 90% methanol, 10% water Example 1

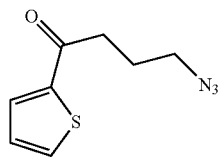

A. 4-Azido-1-thiophen-2-yl-butan-1-one

A mixture of 4-chloro-2'-butyrothienone (3.0 g, 15.9 mmol) and sodium azide (2.07 g, 31.8 mmol) in DMF (50 mL) was stirred at 70° C. for 1.5 h. The reaction mixture was then partitioned between ethyl acetate (200 mL) and water (200 mL). The organic layer was washed with water (100 mL), saturated aqueous sodium bicarbonate (100 mL) and brine (100 mL) and dried over sodium sulfate. Removal of the solvent in vacuum provided the title compound (2.58 g, 83% yield). MS m/e 218; HPLC retention time 0.85 min (Method B).

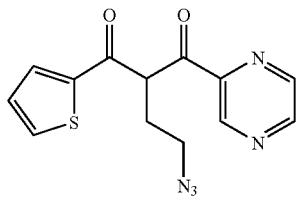

B. 2-(2-Azido-ethyl)-1-pyrazin-2-yl-3-thiophen-2-yl-propane-1,3-dione

A suspension of pyrazine 2-carboxylic acid (2.52 g, 20.3 mmol) in dichloromethane (30 mL) at 0° C. was treated with oxalyl chloride (1.95 mL, 22.3 mmol) followed by the addition of catalytic DMF (1 drop). The reaction mixture was allowed to warm to room temperature overnight, then concentrated in vacuo to give pyrazine 2-carbonyl chloride as a violet-colored solid.

In a separate reaction flask, LHMDS (1.0 M in THF, 11.28 mL) was added drop wise to a solution of the ketene 1A (1.10 g, 5.64 mmol) in THF (10 mL) at −78° C. The reaction mixture was maintained at that temperature for 20 min. The pyrazine 2-carbonyl chloride (1.0 g, 5.64 mmol) was then rapidly introduced as a solid to the reaction mixture to give a dark brown solution which was maintained at −78° C. for another 20 min. The reaction mixture was then partitioned between ethyl acetate and saturated aqueous ammonium chloride. The organic layer was washed with saturated aqueous sodium bicarbonate and brine, dried over sodium sulfate, then concentrated to give the crude oil. Purification by flash column chromatography (silica, 30% ethyl acetate in hexanes) provided the title compound as a yellow oil (939 mg, 55% yield). MS m/e 324; HPLC retention time 2.78 min (Method A).

$^1$H NMR (400 MHz, CDCl$_3$): δ 2.36 (m, 1 H), 2.58 (m, 1 H), 3.60 (dd, 2 H), 5.82 (dd, 1 H), 7.28 (dd, 1 H), 7.82 (d, 1 H), 8.07 (d, 1 H), 8.67 (s, 1 H), 8.88 (s, 1 H), 9.37 (s, 1 H).

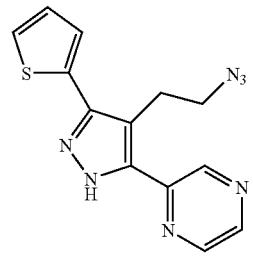

C. 2-[4-(2-Azido-ethyl)-5-thiophen-2-yl-2H-pyrazol-3-yl]-pyrazine

A solution of the dione 1B (213 mg, 0.71 mmol), hydrazine monohydrate (0.17 mL, 3.54 mmol) and concentrated aqueous HCl (1 drop) in methanol (4 mL) was heated at 70° C. for 1 h. The reaction mixture was then concentrated to give a yellow sticky solid which was purified by flash column chromatography (silica, 1:1 ethyl acetate:hexanes) to give the title compound (142 mg, 67% yield) as a colorless oil. MS m/e 298; HPLC retention time 3.40 min (Method A).

$^1$H NMR (400 MHz, CDCl$_3$): δ 3.29 (t, 2 H), 3.58 (t, 2 H), 7.13 (dd, 1 H), 7.41 (m, 2 H), 8.45 (d, 1 H), 8.59 (b s, 1 H), 9.25 (s, 1 H).

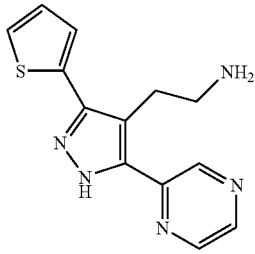

D. 2-(5-Pyrazin-2-yl-3-thiophen-2-yl-1H-pyrazol-4-yl)-ethylamine

A mixture of the azide 1C (140 mg, 0.47 mmol), and palladium on carbon (10% w/w, 30 mg) in methanol (5 mL) was stirred under an atmosphere of hydrogen gas (1 atm, balloon) for 3 h. The reaction mixture was then flushed with nitrogen and the mixture filtered over celite. Concentration under reduced pressure gave the title compound (104 mg, 82% yield) as a yellow oil. MS m/e 272; HPLC retention time 1.57 min (Method A).

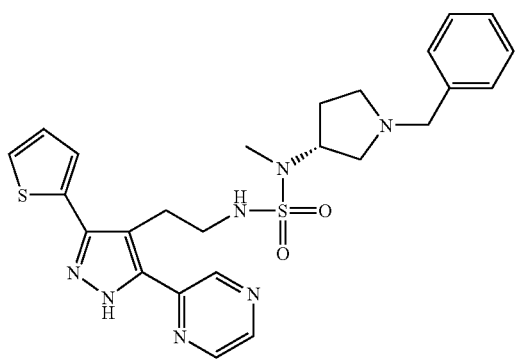

E.

2-Chloroethanol (0.095 mL, 1.41 mmol) was added dropwise to a solution of chlorosulfonyl isocyanate (0.122 mL, 1.41 mmol) in dichloromethane at −20° C. The reaction mixture was warmed to 0° C. and maintained at that temperature 1.5 h. The solution was then transferred by canula to a solution of the amine XX (383 mg, 1.41 mmol) and triethylamine (1.38 ml, 9.9 mmol) in dichloromethane at −10° C. The reaction mixture was then stirred 17 h at room temperature under nitrogen to give a clear olive-green solution.

A portion of the solution of intermediate sulfamolyoxazolidinone was concentrated to give a greenish solid (30 mg) which was taken up in acetonitrile (3 mL) and treated with triethylamine (0.059 mL, 0.42 mmol) and R-(1-benzyl-pyrrolidin-3-yl)-methyl-amine (0.013 mL, 0.046 mmol). The reaction mixture was heated at 70° C. 16 h, then concentrated and purified by reverse phase preparative HPLC to provide 25 mg of the title compound. MS m/e 525; HPLC retention time 2.31 min (Method A).

$^1$H NMR (CD$_3$OD): δ 1.95 (b s, 2H), 2.52 (b s, 2 H), 3.00 (s, 3 H), 3.10-3.40 (b m, 5 H), 4.15 (b s, 2 H), 4.20-4.40 (b m, 2 H), 6.96 (dd, 1 H), 7.20 (d, 1 H), 7.25 (m, 5 H), 7.33 (d, 1 H), 8.31 (s, 1 H), 8.44 (s, 1 H), 8.93 (s, 1 H).

$^1$H NMR (CDCl$_3$): δ 0.83 (t, 3H), 1.3 (dd, 2H), 1.39 (s, 9H), 1.40 (t, 2H), 1.45 (bm, 2H), 1.75 (bs, 2H), 2.1 (bs, 2H), 2.4 (bs, 2H), 2.76 (s, 3H)

Examples 2 to 26

Examples 2 to 26 were prepared following the procedures described for the preparation of 1.

| Example # | Structure | Rt (min) | Analytical HPLC Method | M/z (MH)$^+$ |
|---|---|---|---|---|
| 2 | 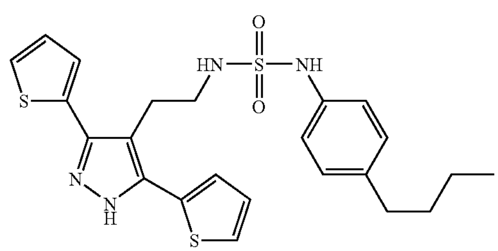 | 3.47 | A | 487 |
| 3 | 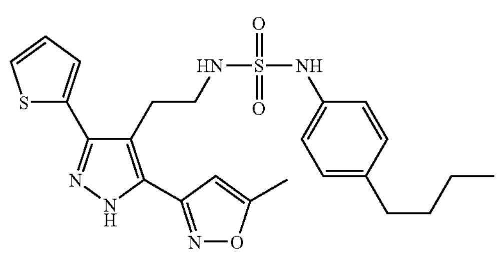 | 1.89 | B | 486 |
| 4 | 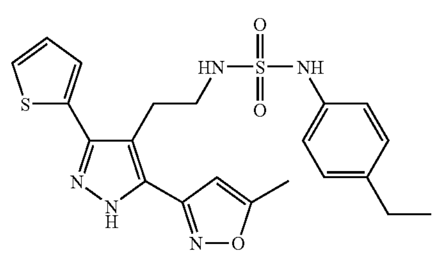 | 1.71 | B | 458 |

-continued

| Example # | Structure | Rt (min) | Analytical HPLC Method | M/z (MH)+ |
|---|---|---|---|---|
| 5 | 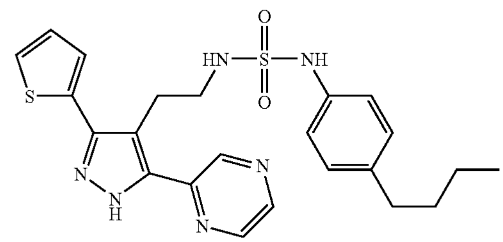 | 3.40 | A | 483 |
| 6 | 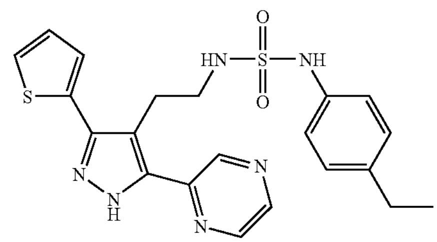 | 3.02 | A | 455 |
| 7 | 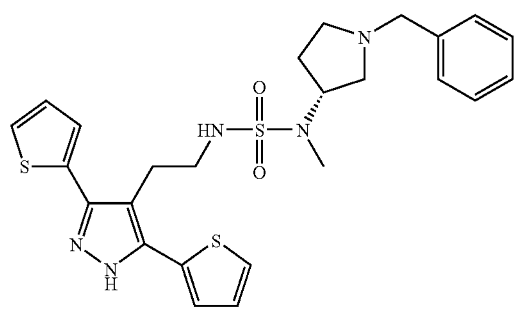 | 2.01 | A | 528 |
| 8 | 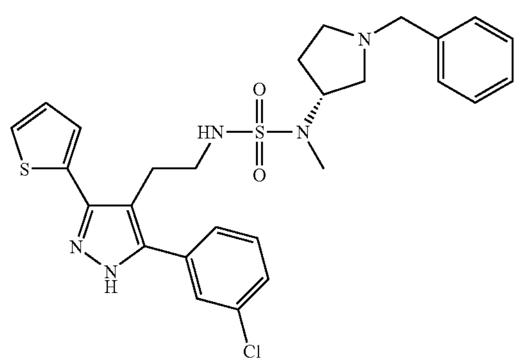 | 2.73 | A | 557 |
| 9 | 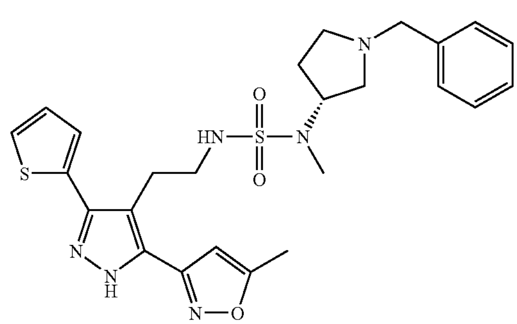 | 2.50 | A | 527 |

| Example # | Structure | Rt (min) | Analytical HPLC Method | M/z (MH)+ |
|---|---|---|---|---|
| 10 | 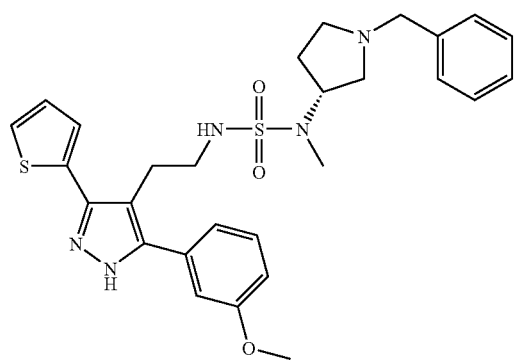 | 2.52 | A | 552 |
| 11 | 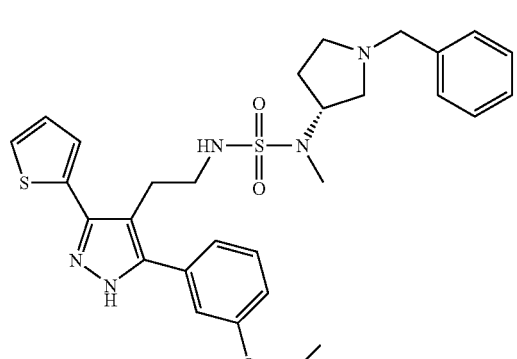 | 2.65 | A | 566 |
| 12 | 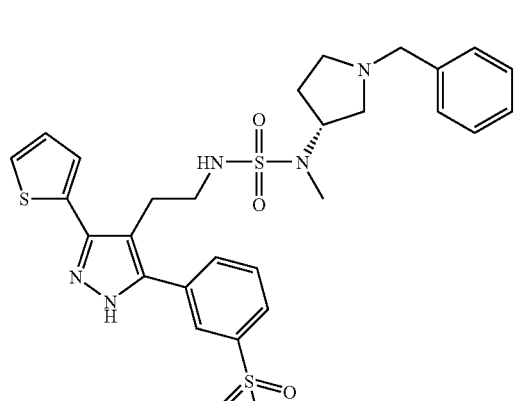 | 2.24 | A | 600 |
| 13 | 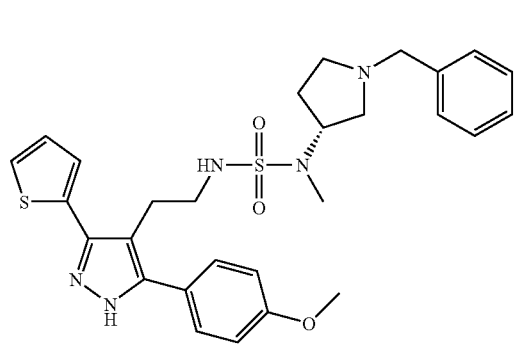 | 2.48 | A | 552 |

-continued

| Example # | Structure | Rt (min) | Analytical HPLC Method | M/z (MH)+ |
|---|---|---|---|---|
| 14 | 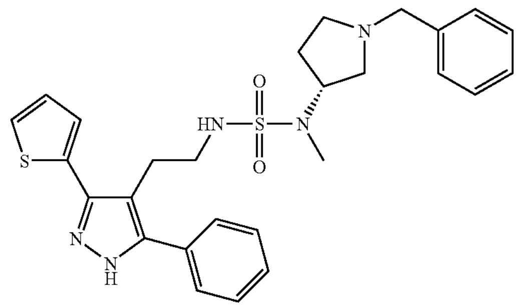 | 2.42 | A | 552 |
| 15 | 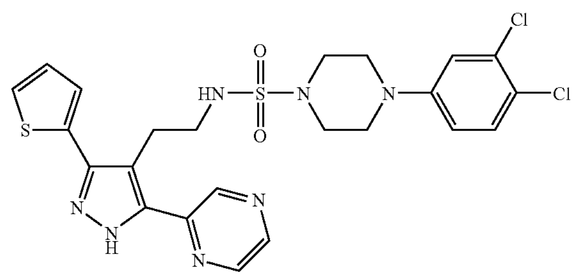 | 3.88 | A | 566 |
| 16 | 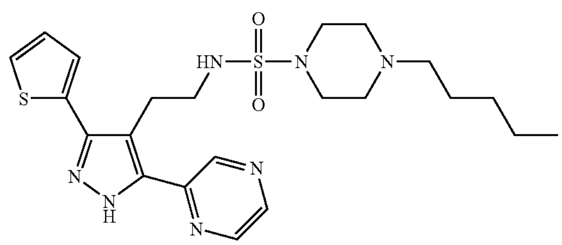 | 2.31 | A | 490 |
| 17 | 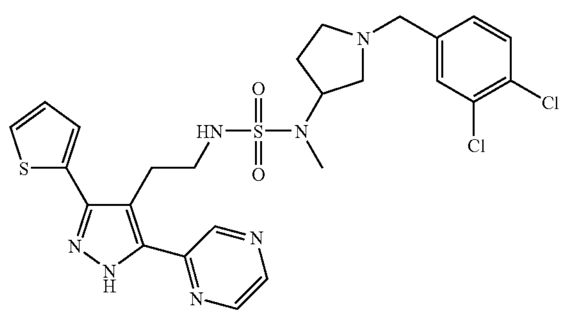 | 2.77 | A | 593 |
| 18 | 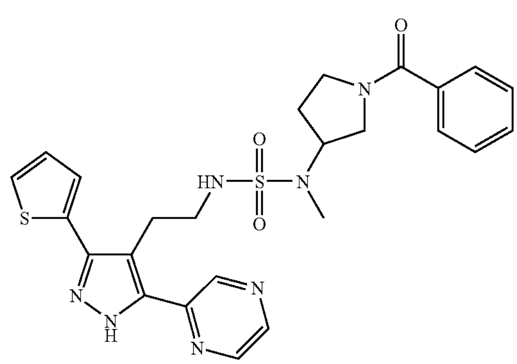 | 2.95 | A | 538 |

-continued

| Example # | Structure | Rt (min) | Analytical HPLC Method | M/z (MH)+ |
|---|---|---|---|---|
| 19 | 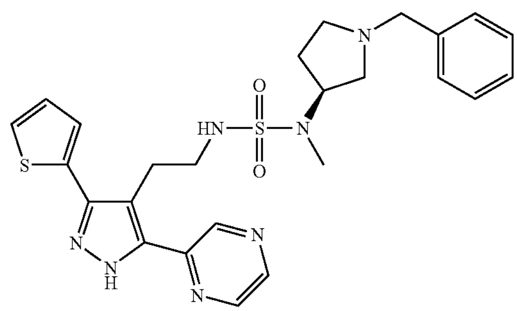 | 2.46 | A | 524 |
| 20 | 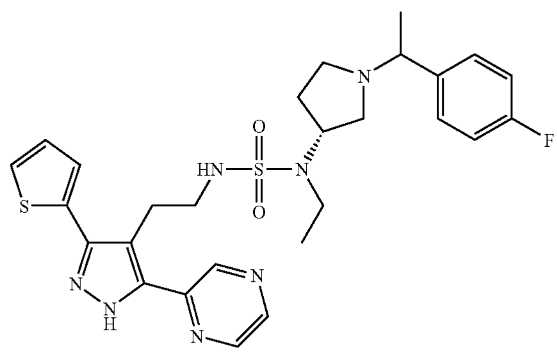 | 2.57 | A | 571 |
| 21 | 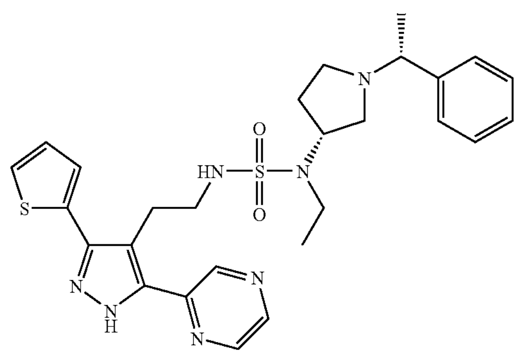 | 2.46 | A | 553 |
| 22 | 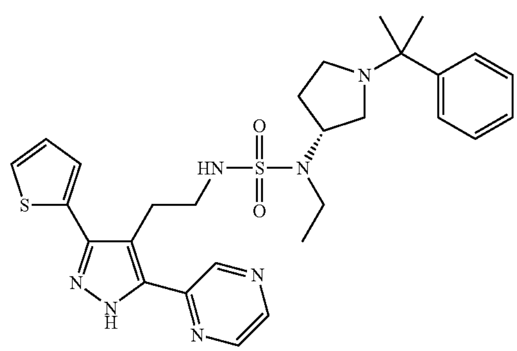 | 2.53 | A | 567 |

-continued

| Example # | Structure | Rt (min) | Analytical HPLC Method | M/z (MH)+ |
|---|---|---|---|---|
| 23 | 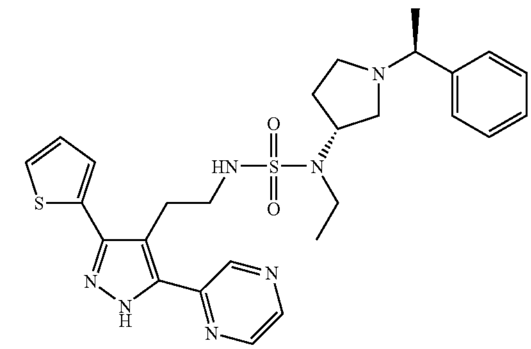 | 2.46 | A | 553 |
| 24 | 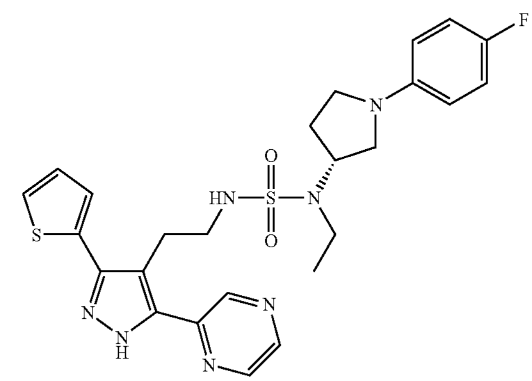 | 3.73 | A | 542 |
| 25 | 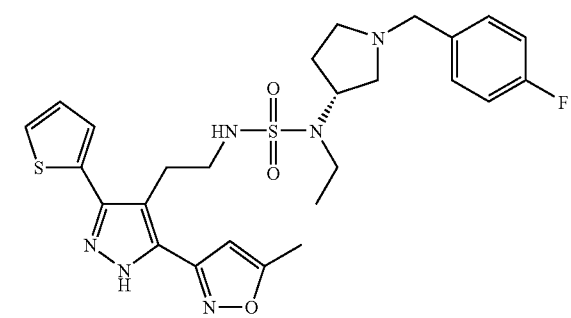 | 1.51 | B | 560 |
| 26 | 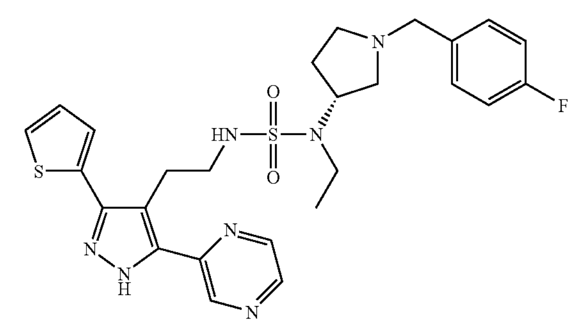 | 2.47 | A | 556 |

Example 27

4-Pentyl-N-[2-(5-pyrazin-2-yl-3-thiophen-2-yl-1H-pyrazol-4-yl)-ethyl]-benzenesulfonamide

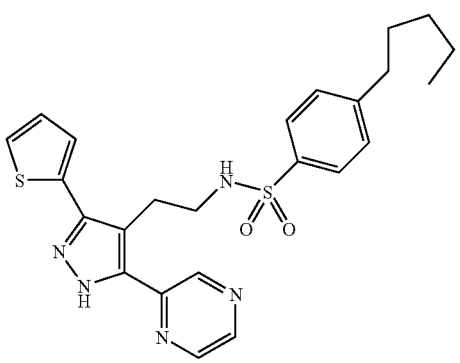

A mixture of the 2-(5-Pyrazin-2-yl-3-thiophen-2-yl-1H-pyrazol-4-yl)-ethylamine 1D (7 mg, 25.8 μmol), diisopropylethylamine (9.0 μl, 51.6 μmol) and 4-n-pentylbenzenesulfonyl chloride (7.0 mg, 28.3 μmol) in dichloromethane (1 mL) was stirred for 3 h. The reaction mixture was concentrated under reduced pressure. The crude product dissolved in methanol (2 ml) and was purified by prep-HPLC. Removal of the solvent in vacuo provided the title compound (3.8 g mg, 41% yield). MS m/e 481; HPLC retention time 3.54 min (Method A).

Examples 28 to 126

The following Examples 28 to 126 were prepared following the same method used for the preparation of 27 from 1D.

| Example # | Structure | Rt (min) | Analytical HPLC Method | M/z (MH)+ |
|---|---|---|---|---|
| 28 | 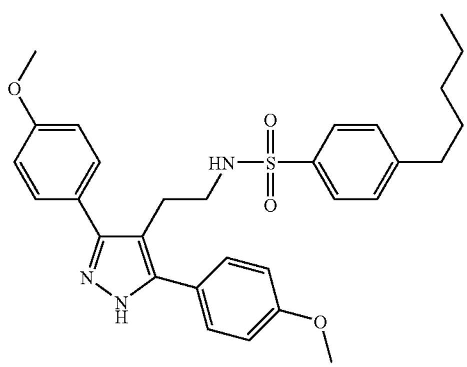 | 3.62 | A | 534 |
| 29 | 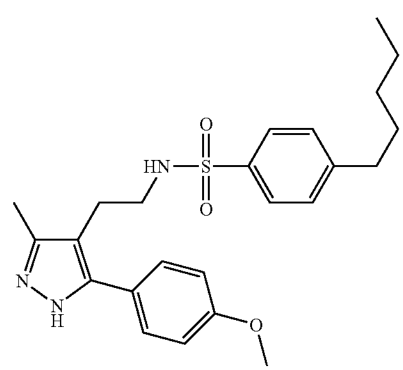 | 3.24 | A | 442 |

-continued

| Example # | Structure | Rt (min) | Analytical HPLC Method | M/z (MH)+ |
|---|---|---|---|---|
| 30 | 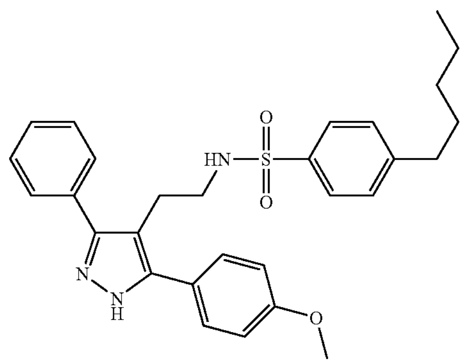 | 3.64 | A | 504 |
| 31 | 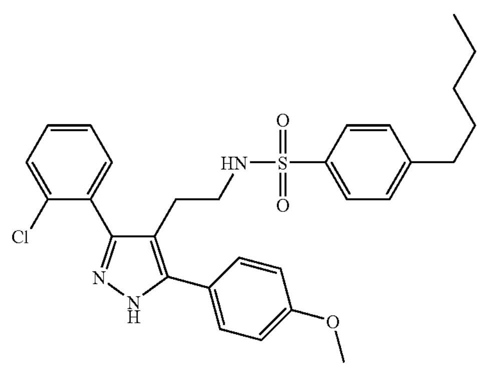 | 3.66 | A | 538 |
| 32 | 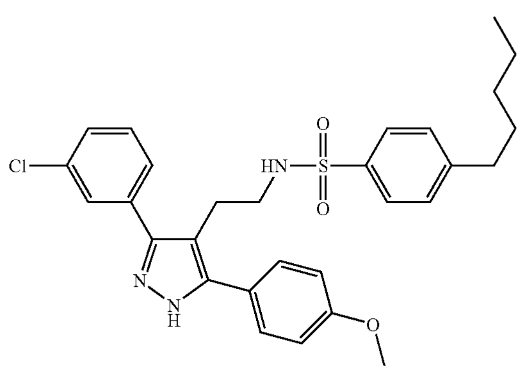 | 3.85 | A | 538 |
| 33 | 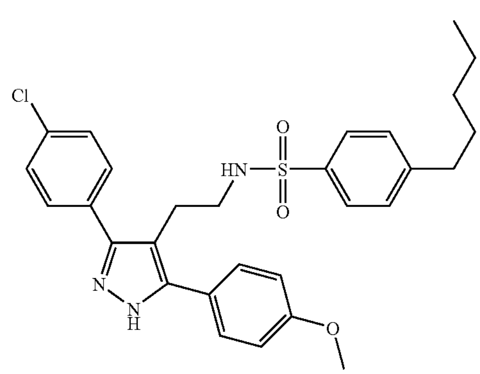 | 3.85 | A | 538 |

| Example # | Structure | Rt (min) | Analytical HPLC Method | M/z (MH)+ |
|---|---|---|---|---|
| 34 | 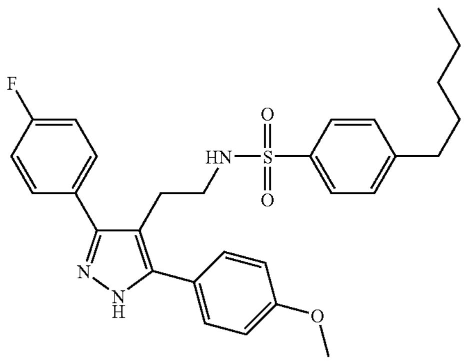 | 3.69 | A | 522 |
| 35 | 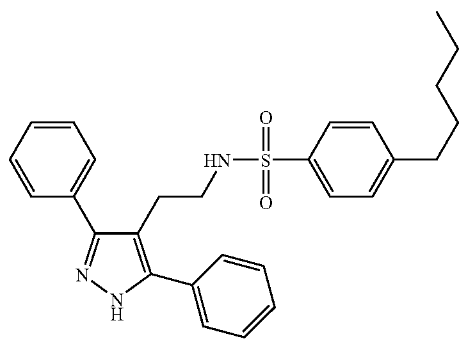 | 3.67 | A | 474 |
| 36 | 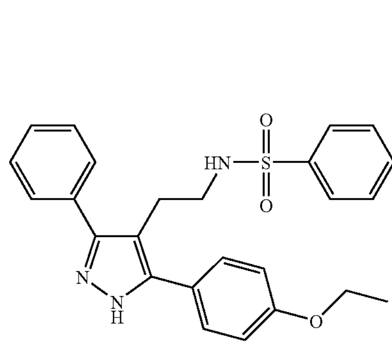 | 3.76 | A | 518 |
| 37 | 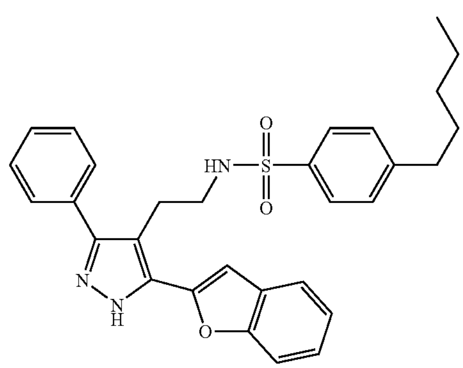 | 3.66 | A | 509 |

-continued

| Example # | Structure | Rt (min) | Analytical HPLC Method | M/z (MH)+ |
|---|---|---|---|---|
| 38 | 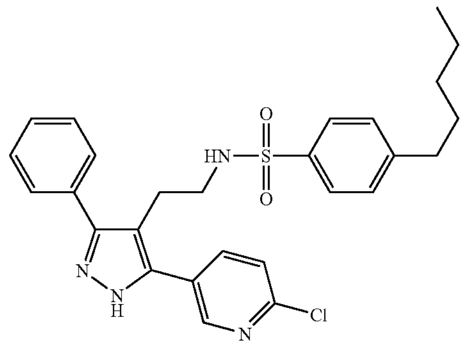 | 3.93 | A | 514 |
| 39 | 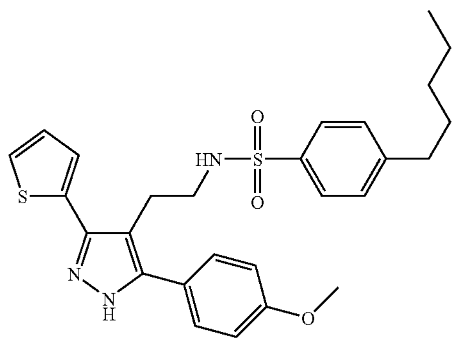 | 3.67 | A | 510 |
| 40 | 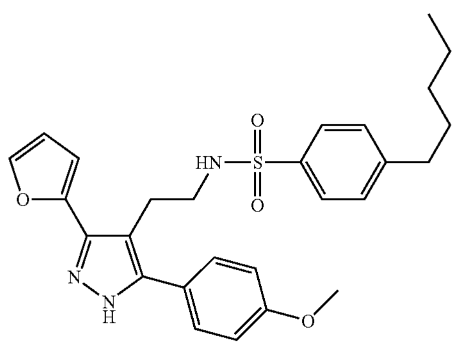 | 3.62 | A | 494 |
| 41 | 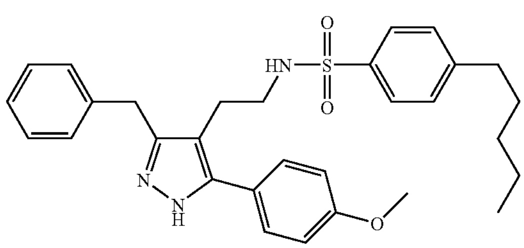 | 3.61 | A | 518 |
| 42 | 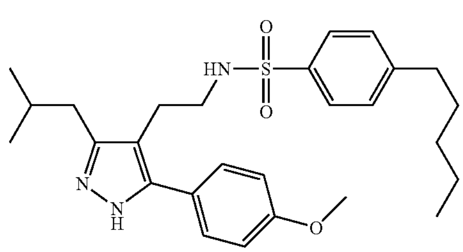 | 3.51 | A | 484 |

-continued

| Example # | Structure | Rt (min) | Analytical HPLC Method | M/z (MH)+ |
|---|---|---|---|---|
| 43 | 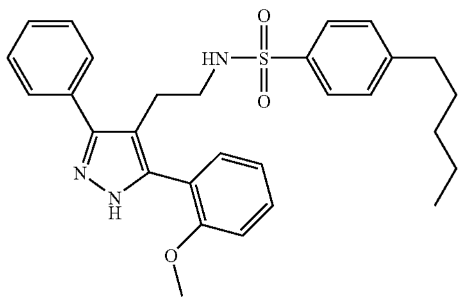 | 3.56 | A | 504 |
| 44 | 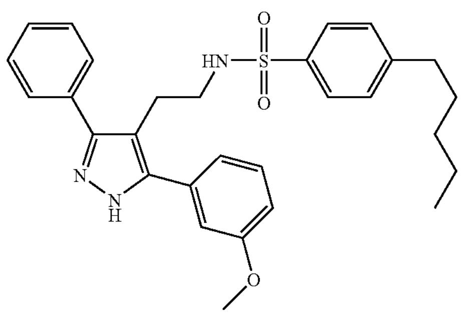 | 3.70 | A | 504 |
| 45 | 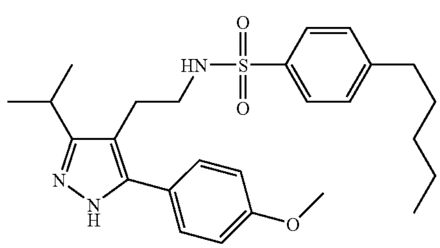 | 3.38 | A | 470 |
| 46 | 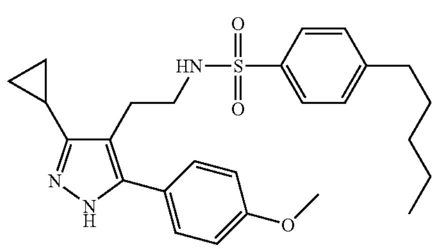 | 3.39 | A | 468 |
| 47 | 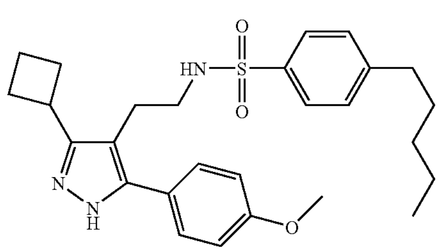 | 3.47 | A | 482 |

-continued

| Example # | Structure | Rt (min) | Analytical HPLC Method | M/z (MH)+ |
|---|---|---|---|---|
| 48 | 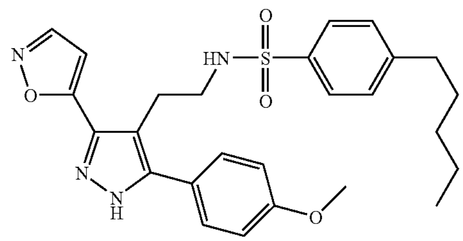 | 3.56 | A | 495 |
| 49 | 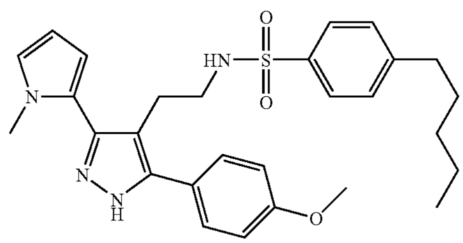 | 3.56 | A | 507 |
| 50 | 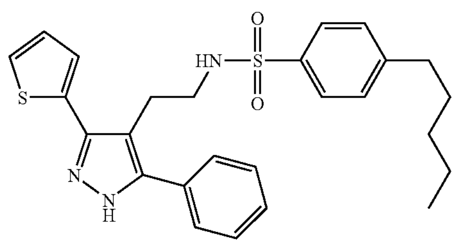 | 3.69 | A | 480 |
| 51 | 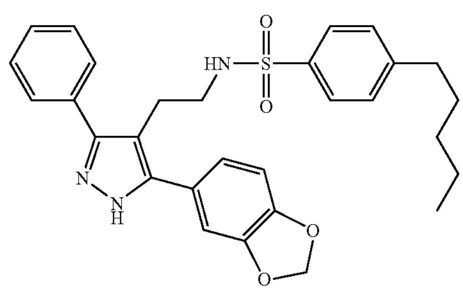 | 3.62 | A | 518 |
| 52 | 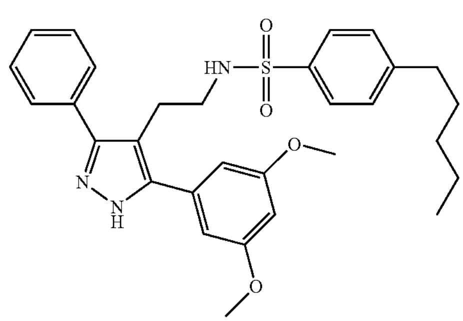 | 3.71 | A | 534 |

| Example # | Structure | Rt (min) | Analytical HPLC Method | M/z (MH)+ |
|---|---|---|---|---|
| 53 | 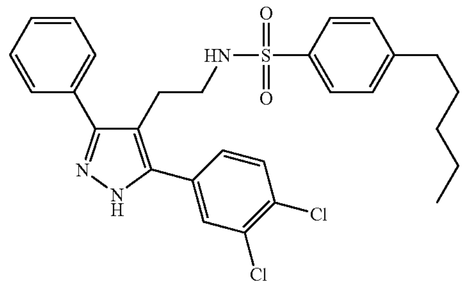 | 3.99 | A | 542 |
| 54 | 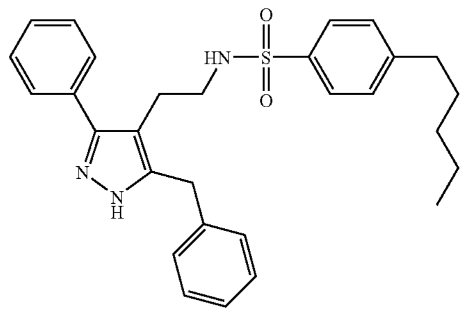 | 3.66 | A | 488 |
| 55 | 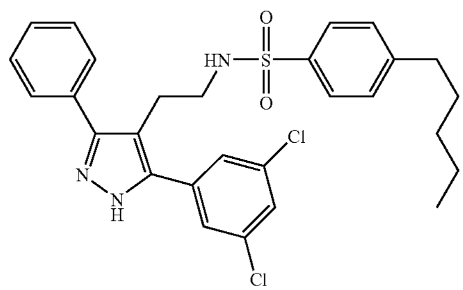 | 4.05 | A | 542 |
| 56 | 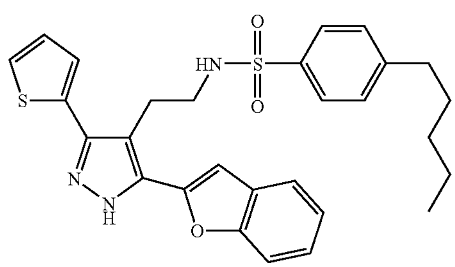 | 3.92 | A | 520 |
| 57 | 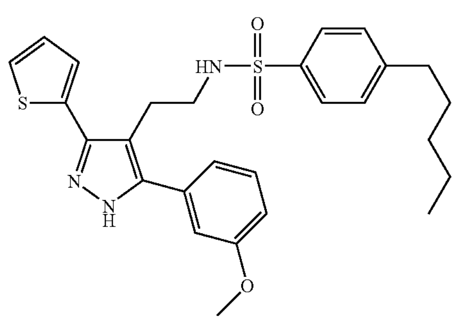 | 3.70 | A | 510 |

-continued

| Example # | Structure | Rt (min) | Analytical HPLC Method | M/z (MH)+ |
|---|---|---|---|---|
| 58 | 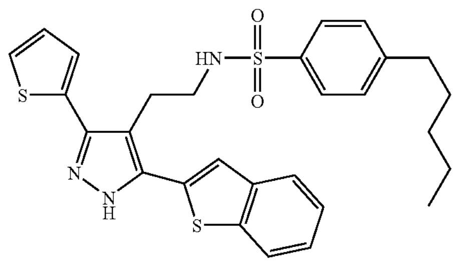 | 3.93 | A | 536 |
| 59 | 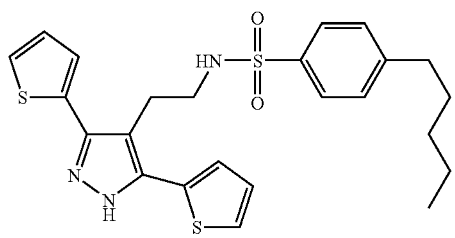 | 3.66 | A | 486 |
| 60 | 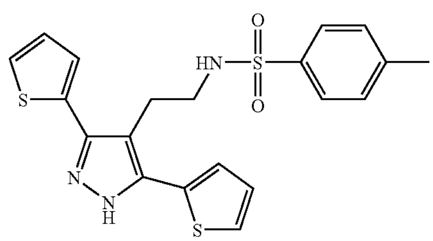 | 2.89 | A | 430 |
| 61 | 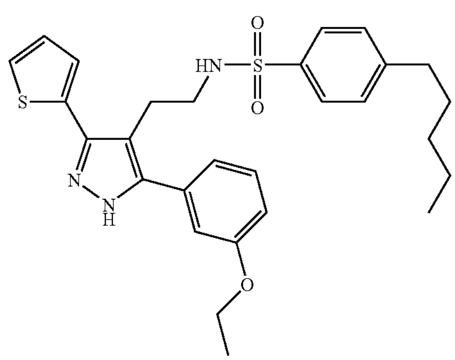 | 3.75 | A | 524 |
| 62 | 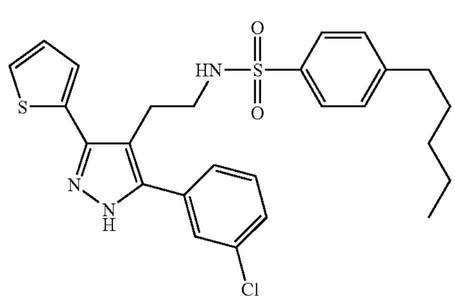 | 3.79 | A | 514 |

-continued

| Example # | Structure | Rt (min) | Analytical HPLC Method | M/z (MH)+ |
|---|---|---|---|---|
| 63 | 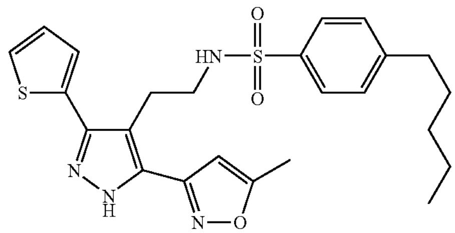 | 3.66 | A | 485 |
| 64 | 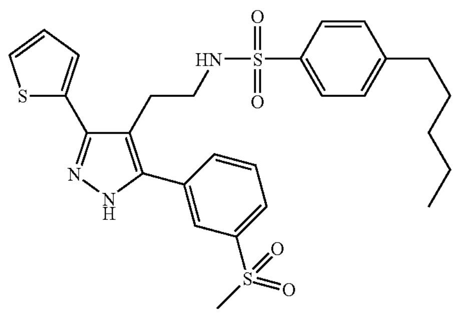 | 3.48 | A | 558 |
| 65 | 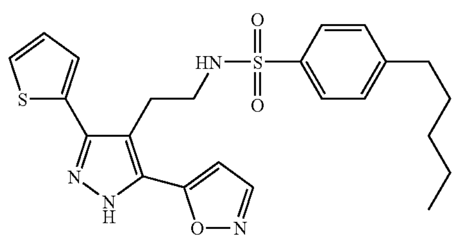 | 3.54 | A | 471 |
| 66 | 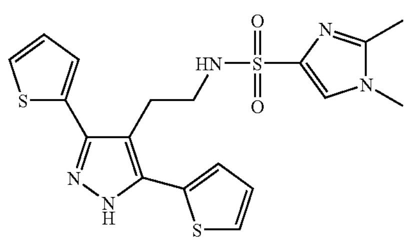 | 2.30 | A | 434 |
| 67 | 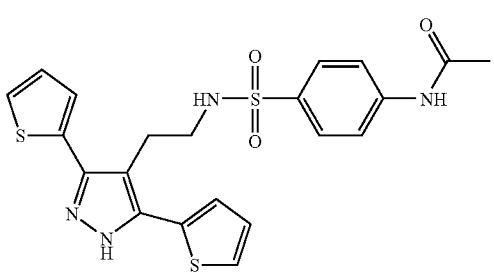 | 2.56 | A | 473 |
| 68 | 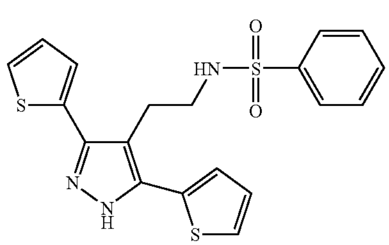 | 2.77 | A | 416 |

-continued

| Example # | Structure | Rt (min) | Analytical HPLC Method | M/z (MH)+ |
|---|---|---|---|---|
| 69 | 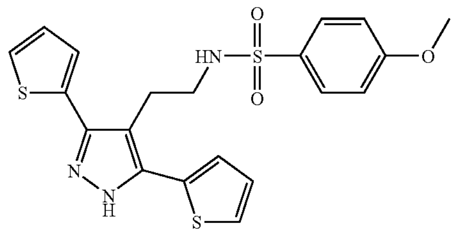 | 2.81 | A | 446 |
| 70 | 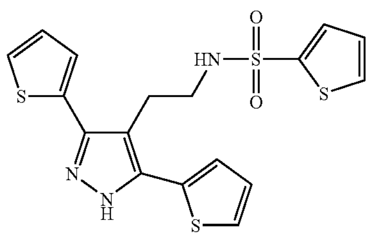 | 2.70 | A | 422 |
| 71 | 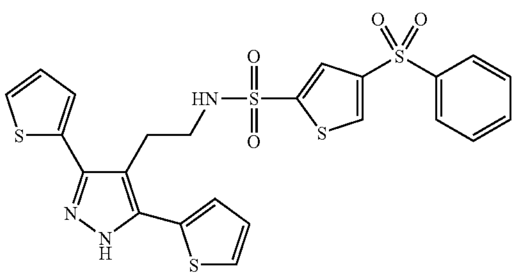 | 2.91 | A | 562 |
| 72 | 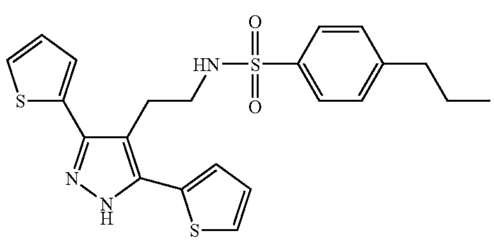 | 3.27 | A | 458 |
| 73 | 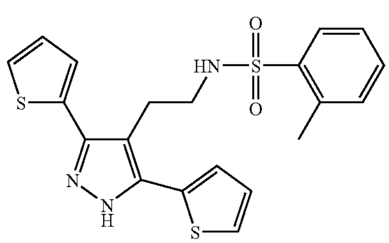 | 2.94 | A | 430 |
| 74 | 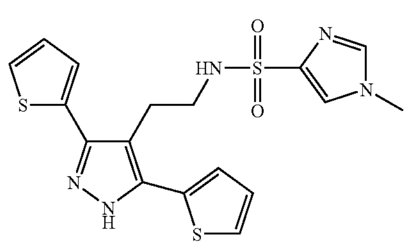 | 2.31 | A | 420 |

-continued

| Example # | Structure | Rt (min) | Analytical HPLC Method | M/z (MH)+ |
|---|---|---|---|---|
| 75 | 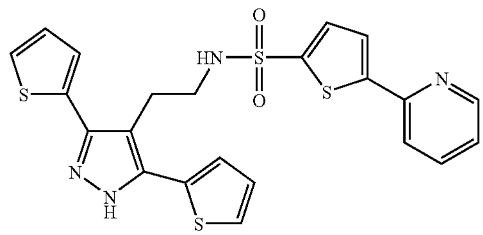 | 2.89 | A | 499 |
| 76 | 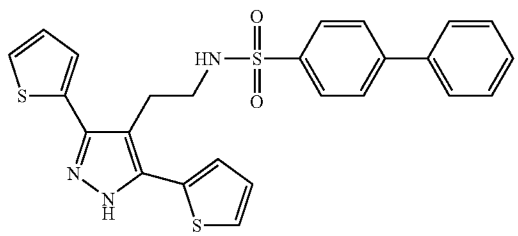 | 3.35 | A | 492 |
| 77 | 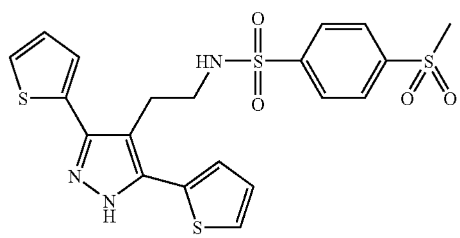 | 2.58 | A | 494 |
| 78 | 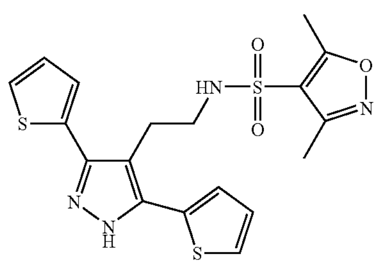 | 2.77 | A | 435 |
| 79 | 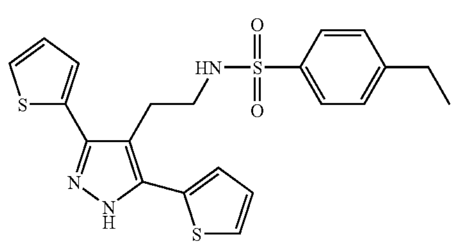 | 3.09 | A | 444 |
| 80 | 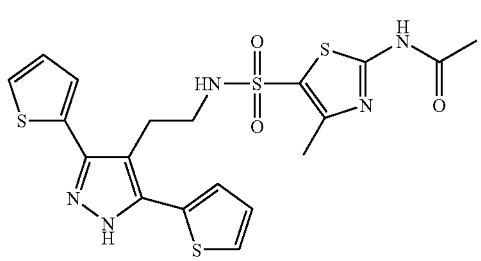 | 2.61 | A | 494 |

-continued

| Example # | Structure | Rt (min) | Analytical HPLC Method | M/z (MH)+ |
|---|---|---|---|---|
| 81 | 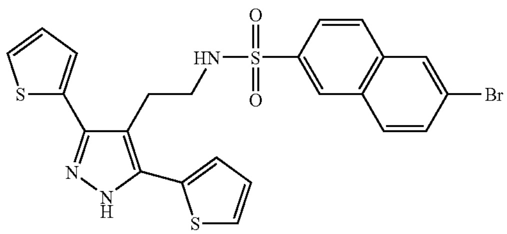 | 3.51 | A | 544 |
| 82 | 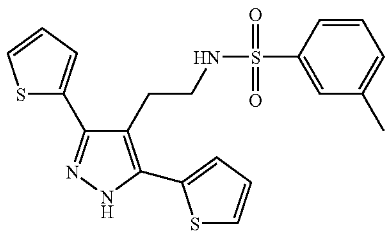 | 2.93 | A | 430 |
| 83 | 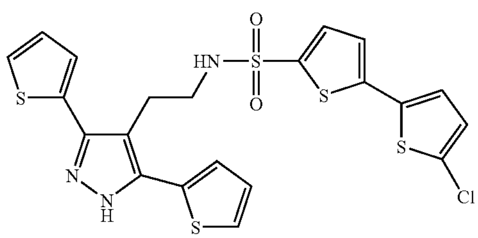 | 3.60 | A | 538 |
| 84 | 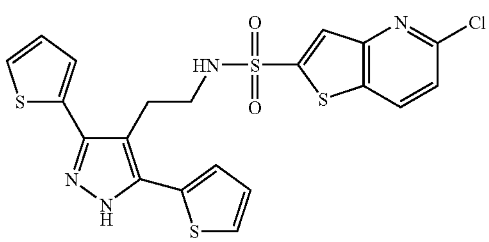 | 3.04 | A | 507 |
| 85 | 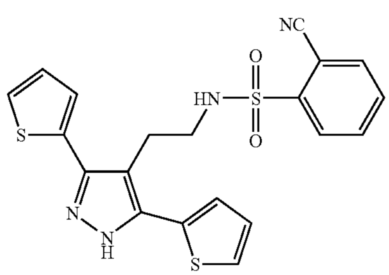 | 2.69 | A | 441 |
| 86 | 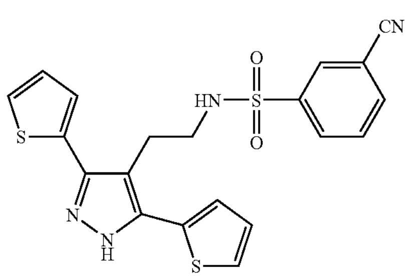 | 2.77 | A | 441 |

-continued
| Example # | Structure | Rt (min) | Analytical HPLC Method | M/z (MH)+ |
|---|---|---|---|---|
| 87 | 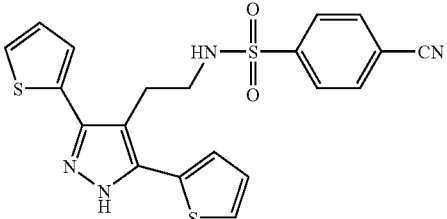 | 2.77 | A | 441 |
| 88 | 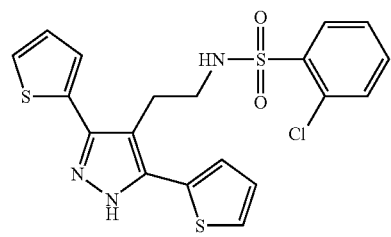 | 2.91 | A | 450 |
| 89 | 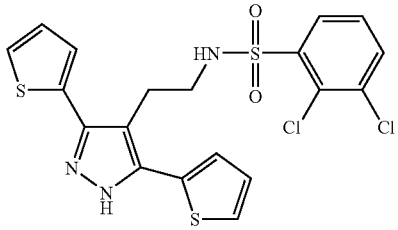 | 3.16 | A | 484 |
| 90 | 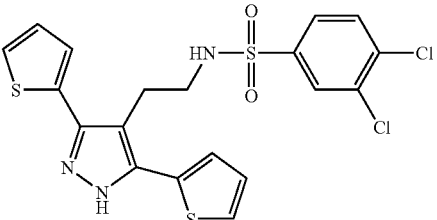 | 3.36 | A | 484 |
| 91 | 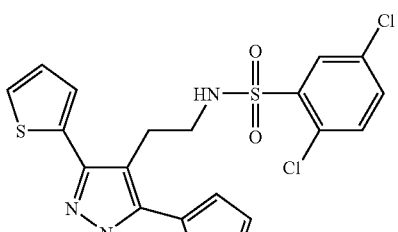 | 3.23 | A | 484 |
| 92 | 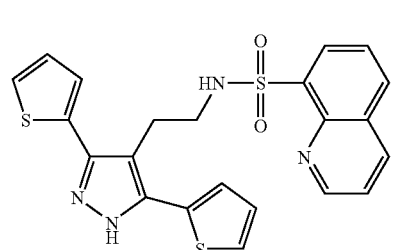 | 2.86 | A | 467 |

| Example # | Structure | Rt (min) | Analytical HPLC Method | M/z (MH)+ |
|---|---|---|---|---|
| 93 | 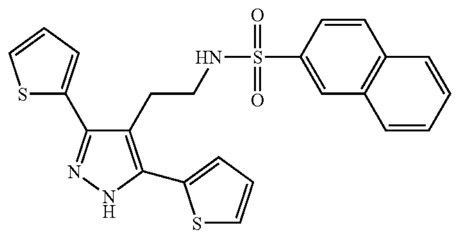 | 3.16 | A | 466 |
| 94 | 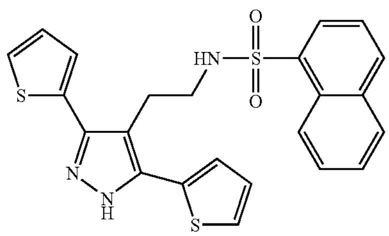 | 3.11 | A | 466 |
| 95 | 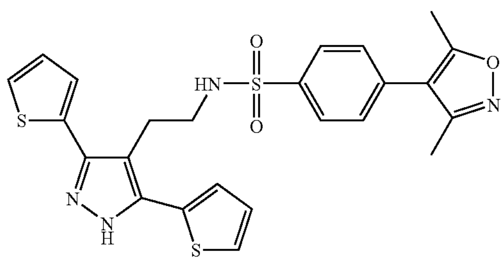 | 2.37 | A | 511 |
| 96 | 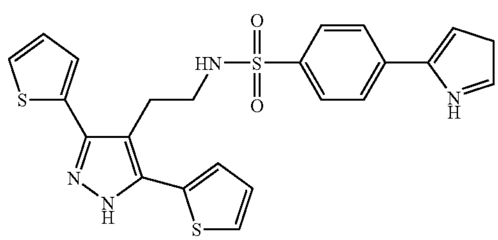 | 2.43 | A | 481 |
| 97 | 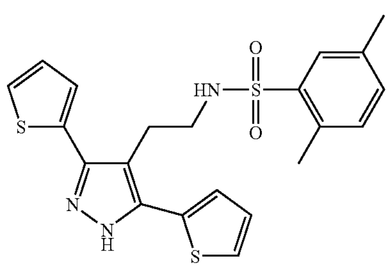 | 3.37 | A | 444 |
| 98 | 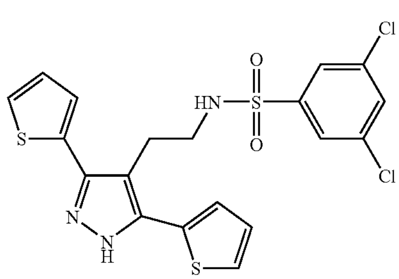 | 3.68 | A | 484 |

-continued

| Example # | Structure | Rt (min) | Analytical HPLC Method | M/z (MH)+ |
|---|---|---|---|---|
| 99 | 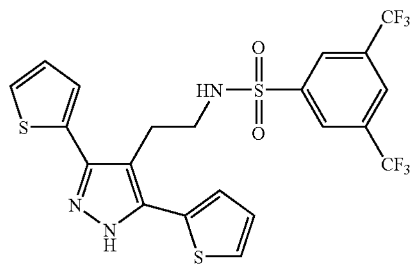 | 3.79 | A | 552 |
| 100 | 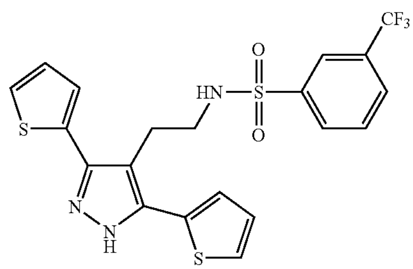 | 1.74 | B | 484 |
| 101 | 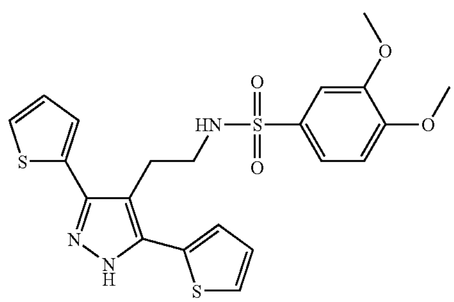 | 1.46 | B | 476 |
| 102 | 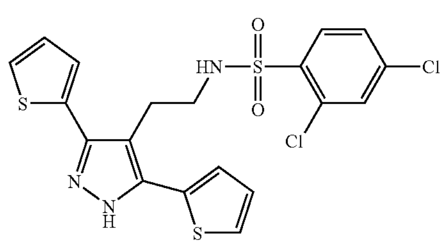 | 1.79 | B | 485 |
| 103 | 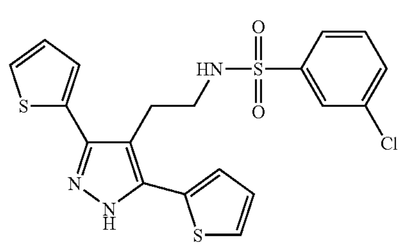 | 3.32 | A | 451 |

-continued

| Example # | Structure | Rt (min) | Analytical HPLC Method | M/z (MH)+ |
|---|---|---|---|---|
| 104 | 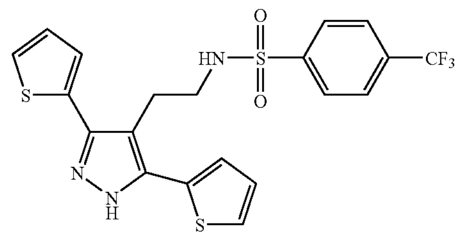 | 3.45 | A | 484 |
| 105 | 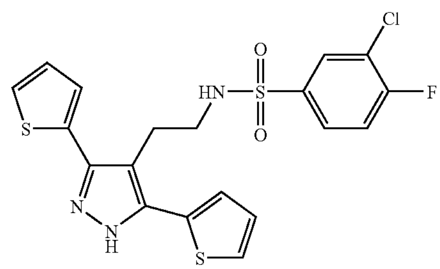 | 1.76 | B | 468 |
| 106 | 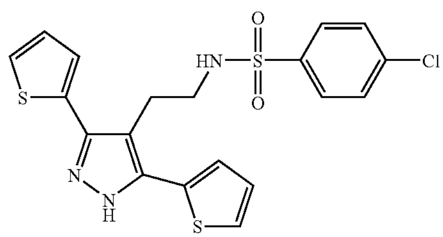 | 3.34 | A | 451 |
| 107 | 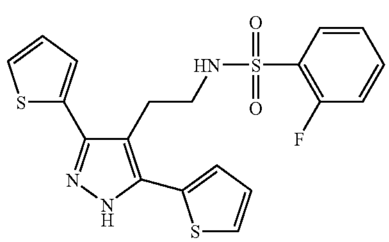 | 3.00 | A | 434 |
| 108 | 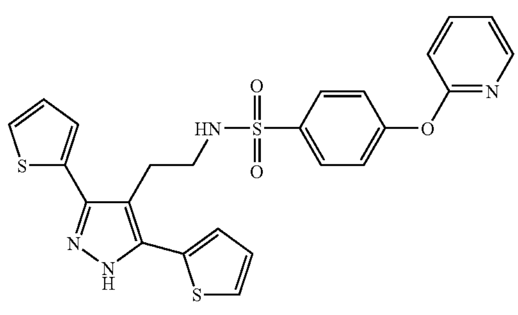 | 1.63 | B | 509 |
| 109 | 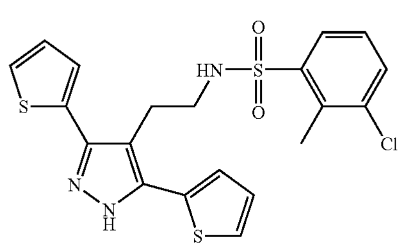 | 1.80 | B | 465 |

-continued

| Example # | Structure | Rt (min) | Analytical HPLC Method | M/z (MH)+ |
|---|---|---|---|---|
| 110 | 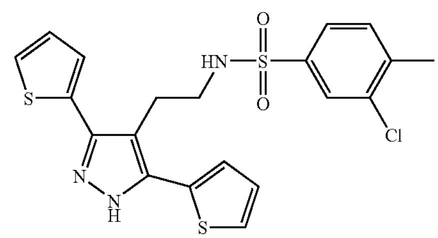 | 1.78 | B | 465 |
| 111 | 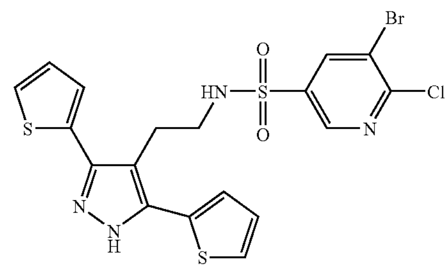 | 1.79 | B | 530 |
| 112 | 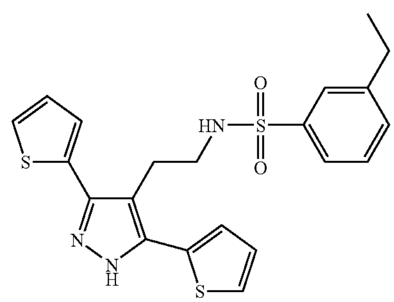 | 3.13 | A | 444 |
| 113 | 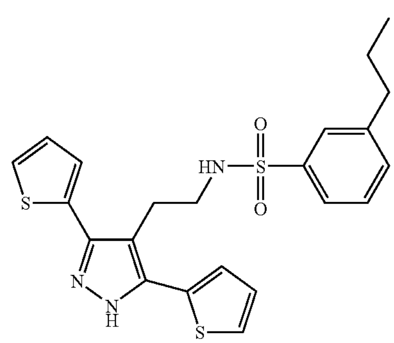 | 3.29 | A | 458 |
| 114 | 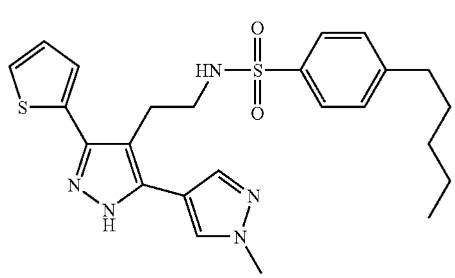 | 3.48 | A | 484 |

| Example # | Structure | Rt (min) | Analytical HPLC Method | M/z (MH)+ |
|---|---|---|---|---|
| 115 | 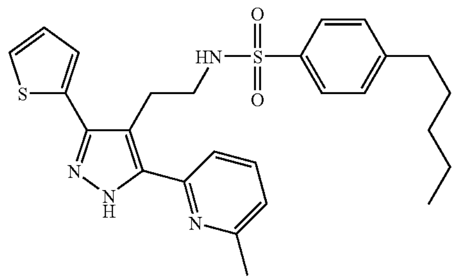 | 3.36 | A | 485 |
| 116 | 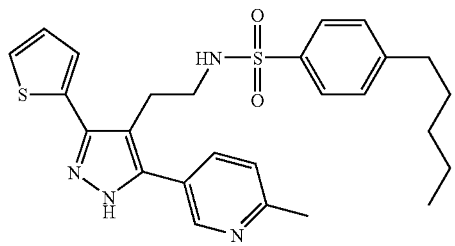 | 3.19 | A | 495 |
| 117 | 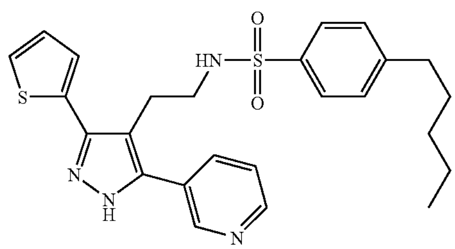 | 3.18 | A | 481 |
| 118 | 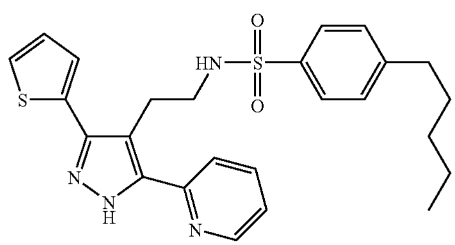 | 3.4 | A | 481 |
| 119 | 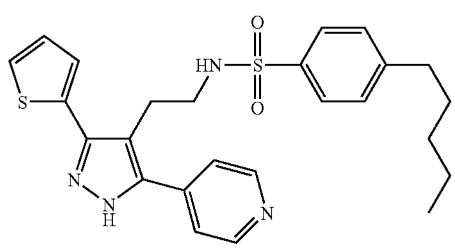 | 3.22 | A | 481 |
| 120 | 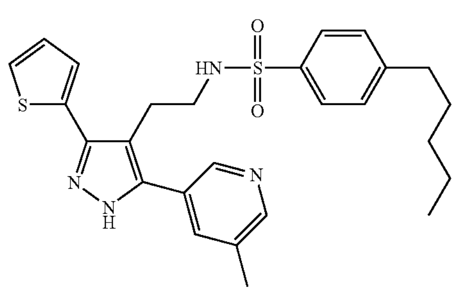 | 3.31 | A | 495 |

-continued

| Example # | Structure | Rt (min) | Analytical HPLC Method | M/z (MH)+ |
|---|---|---|---|---|
| 121 | 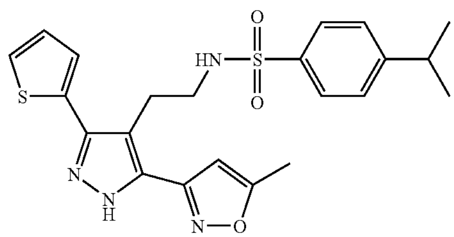 | 3.26 | A | 457 |
| 122 | 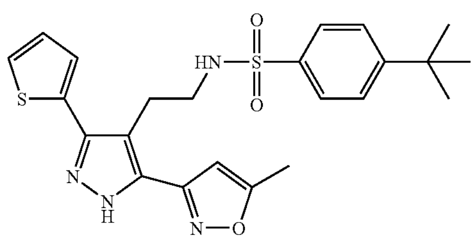 | 3.38 | A | 471 |
| 123 | 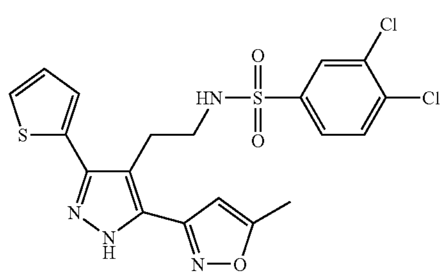 | 3.33 | A | 484 |
| 124 | 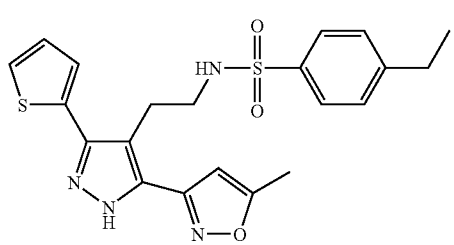 | 3.12 | A | 443 |

-continued

| Example # | Structure | Rt (min) | Analytical HPLC Method | M/z (MH)+ |
|---|---|---|---|---|
| 125 | 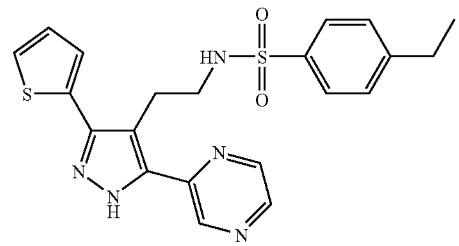 | 3.01 | A | 440 |
| 126 | 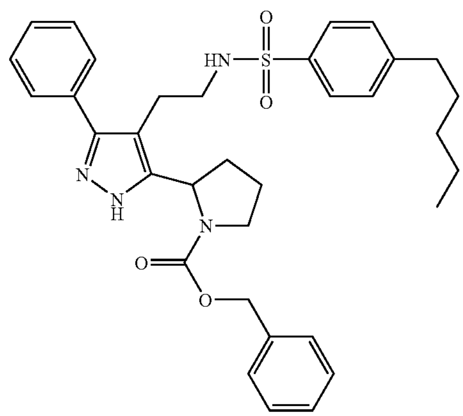 | 3.72 | A | 601 |

Example 127

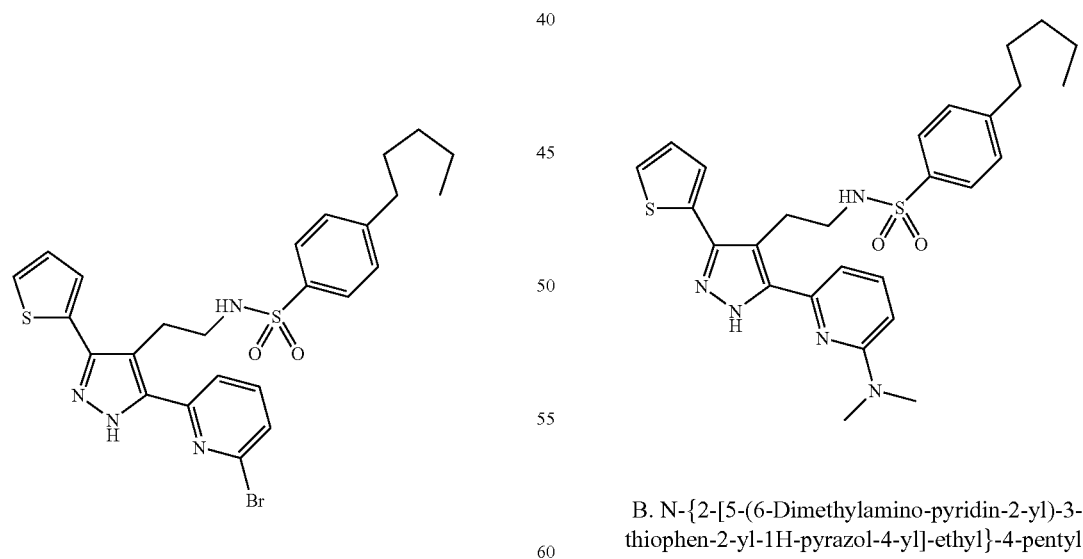

A. N-{2-[5-(6-Bromo-pyridin-2-yl)-3-thiophen-2-yl-1H-pyrazol-4-yl]-ethyl}-4-pentyl-benzenesulfonamide The title compound was prepared following the procedures described for the preparation of Example 27.

B. N-{2-[5-(6-Dimethylamino-pyridin-2-yl)-3-thiophen-2-yl-1H-pyrazol-4-yl]-ethyl}-4-pentyl-benzenesulfonamide A mixture of N-{2-[5-(6-Bromo-pyridin-2-yl)-3-thiophen-2-yl-1H-pyrazol-4-yl]-ethyl}-4-pentyl-benzene-sulfonamide (5 mg, 8.9 μmol) and dimethylamine (2.0M in MeOH, 8.0 ml) in 1-methyl-2-pyrrolidinone (500 μL) was stirred at 190° C. in a seal tube for 3 h. The reaction mixture was concentrated to 2 ml. The crude product was purified by Prep-HPLC. Removal of the solvent in vacuo provided the title compound (1.2 mg, 26% yield). MS m/e 524; HPLC retention time 3.34 min (Method A).

Examples 128 to 135

The following Examples 128 to 135 were prepared following the procedures described for the preparation of Example 127.

| Example # | Structure | Rt (min) | Analytical HPLC Method | M/z (MH)+ |
|---|---|---|---|---|
| 128 | 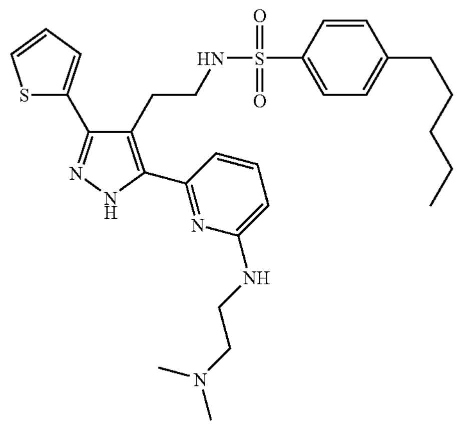 | 3.32 | A | 566 |
| 129 | 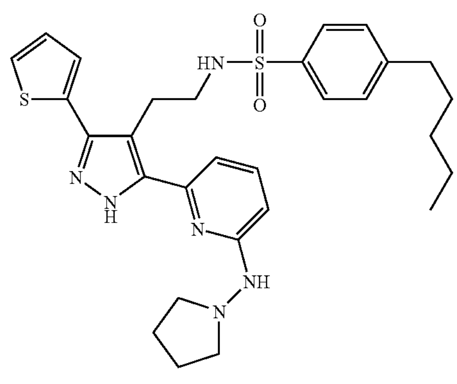 | 3.37 | A | 565 |
| 130 | 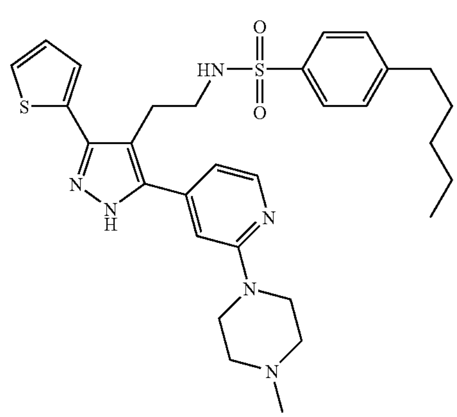 | 3.19 | A | 549 |

-continued

| Example # | Structure | Rt (min) | Analytical HPLC Method | M/z (MH)+ |
|---|---|---|---|---|
| 131 | 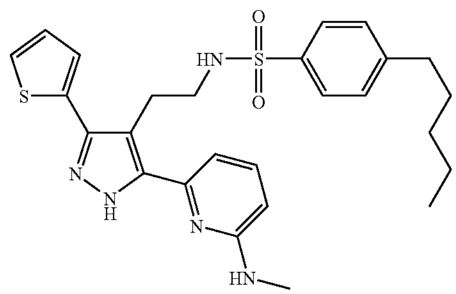 | 3.23 | A | 510 |
| 132 | 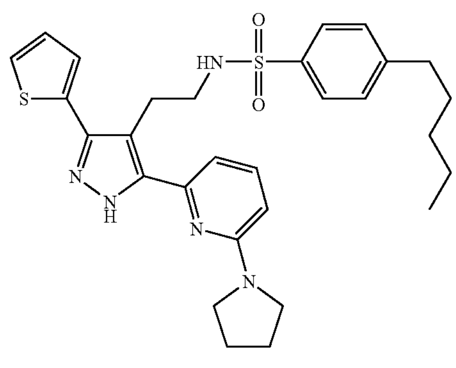 | 3.37 | A | 550 |
| 133 | 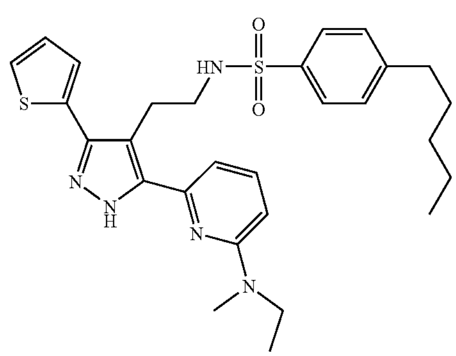 | 3.37 | A | 538 |

| Example # | Structure | Rt (min) | Analytical HPLC Method | M/z (MH)+ |
|---|---|---|---|---|
| 134 | 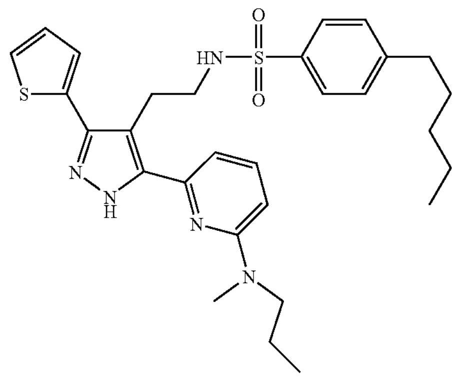 | 3.45 | A | 552 |
| 135 | 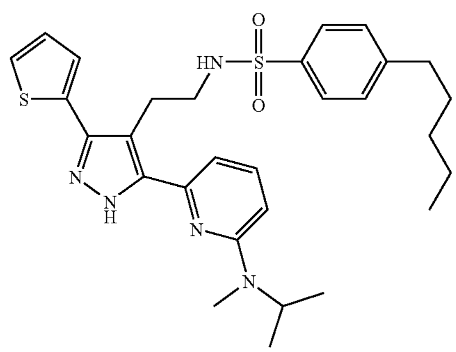 | 3.43 | A | 552 |

Example 136

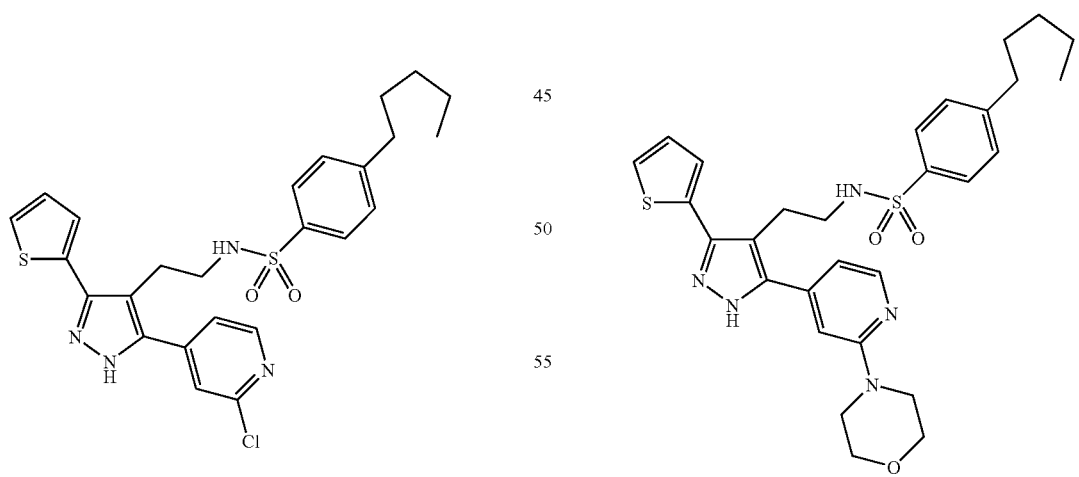

A. N-{2-[5-(2-Chloro-pyridin-4-yl)-3-thiophen-2-yl-1H-pyrazol-4-yl]-ethyl}-4-pentyl-benzenesulfonamide The title compound was prepared following the procedures described for the preparation of Example 27.

B. N-{2-[5-(2-Morpholin-4-yl-pyridin-4-yl)-3-thiophen-2-yl-1H-pyrazol-4-yl]-ethyl}-4-pentyl-benzene sulfonamide A mixture of N- {2-[5-(2-Chloro-pyridin-4-yl)-3-thiophen-2-yl-1H-pyrazol-4-yl]-ethyl}-4-pentyl-benzenesulfonamide (10 mg, 19.4 μmol) and morpholine (17 μl, 194 μmol) in 1-methyl-2-pyrrolidinone (500 μL) was stirred at 190° C. in a seal tube for 3 h. The reaction mixture was concentrated to 2 ml. The crude product was purified by Prep-HPLC. Removal of the solvent in vacuo provided the title compound (8.3 mg, 76% yield). MS m/e 566; HPLC retention time 3.35 min (Method A).

Example 137

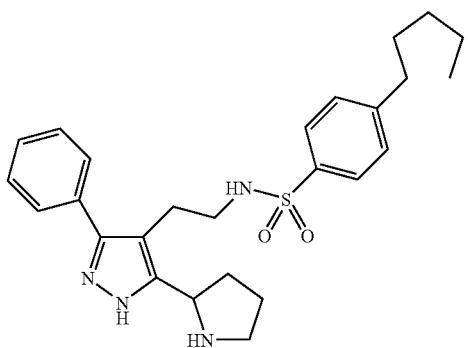

A mixture of Example 126 (4 mg, 6.5 μmol) and palladium on carbon (10% w/w, 1 mg) in methanol (5 mL) was stirred under an atmosphere of hydrogen gas (1 atm, balloon) for 5 h. The reaction mixture was then flushed with nitrogen and the mixture filtered over celite. The filtrate was concentrated. The crude product was dissolved in methanol (2 ml) and was purified by prep-HPLC. Removal of the solvent in vacuo provided the title compound (2.84 mg, 92% yield). MS m/e 467; HPLC retention time 3.22 min (Method A).

$^1$H NMR (CDCl$_3$): δ 9.72(br-s, 1H), 9.16(br-s, 1H), 7.67(d, 2H), 7.41(m, 5H), 7.26(d, 2H), 5.07(m, 1H), 3.61(m, 2H), 3.23(m, 1H), 2.84(m, 3H), 2.63(t, 2H), 2.44(m, 3H), 2.23(m, 1H), 1.59(m, 2H), 1.31(m, 4H), 0.88(t, 3H).

Example 138

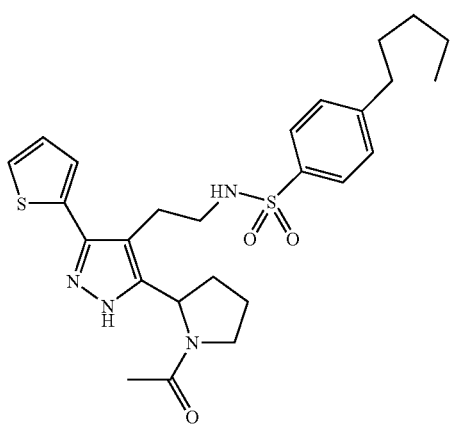

A mixture of Example 137 (4 mg, 8.5 μmol), pyridine (20.6 μl, 255 μmol) and acetic anhydride (20.0 μl, 212 μmol) in THF (1.0 ml) was stirred for 3 h. The mixture was diluted with methanol (1 ml) and the crude product was purified by perp-HPLC. Removal of the solvent in vacuo provided the title compound (2.32 mg, 54% yield). MS m/e 508. HPLC retention time 3.46 min (Method A).

$^1$H NMR (CDCl$_3$): δ 7.71(d, 2H), 7.45(m, 5H), 7.26(d, 2H), 6.69(br-s, 1H), 5.49(m, 1H), 4.04(m, 1H), 3.65(q, 1H), 3.36(m, 1H), 2.94(m, 2H), 2.63(t, 2H), 2.42(m, 1H), 2.18(br-s, 6H), 1.97(m, 2H), 1.62(m, 2H), 1.31(m, 4H), 0.88(t, 3H).

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:
1. A compound according to Formula I

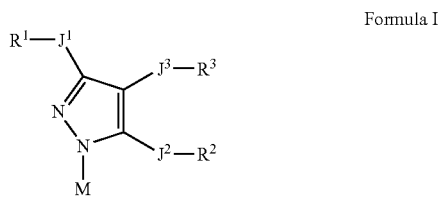

Formula I including enantiomers, diastereomers, salts and solvates thereof, wherein:

J$^1$ is a bond, —C(O)—, —OC(O)—, —C(O)O—, —NR$^4$—, —NR$^4$—C(O)—, or —C(O)NR$^4$—;

J$^2$ is a bond, —C(O)—, —OC(O)—, —C(O)O—, —NR$^{4a}$—, —NR$^{4a}$—C(O)—, or —C(O)NR$^{4a}$—;

J$^3$ is alkylene, cycloalkylene, alkenylene or alkynylene each of which may be optionally substituted with T$^{1a}$, T$^{2a}$ and T$^{3a}$.

M is
(1) hydrogen; or
(2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally substituted with T$^{1b}$, T$^{2b}$ and T$^{3b}$;

R$^1$ is
(1) hydrogen; or
(2) alkyl, alkenyl, alkynyl, cycloalkyl, heterocyclo, aryl, heteroaryl,(cycloalkyl)alkyl, (heterocyclo)alkyl, (aryl)alkyl or (heteroaryl)alkyl each of which may be optionally substituted with T$^{1c}$, T$^{2c}$ and T$^{3c}$;

R$^2$ is
alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally substituted with T$^{1d}$, T$^{2d}$ and T$^{3d}$;

R$^3$ is —NR$^{3a}$SO$_2$Z,

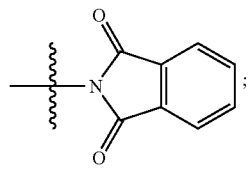

$R^{3a}$, $R^4$, and $R^{4a}$ are each independently
  (1) hydrogen; or
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally independently substituted with $T^{1e}$, $T^{2e}$ and $T^{3e}$;

Z is
  (1) —$NR^5R^6$; or
  (2) alkyl, cycloalkyl, heterocyclo, aryl, heteroaryl, (cycloalkyl)alkyl, (heterocyclo)alkyl, (aryl)alkyl or (heteroaryl)alkyl, each of which may be optionally substituted with $T^{1f}$, $T^{2f}$ and $T^{3f}$;

$R^5$ and $R^6$ are independently
  (1) hydrogen;
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally independently substituted with $T^{1g}$, $T^{2g}$ and $T^{3g}$; or
  (3) —$C(O)R^7$, —$C(O)OR^7$, or —$OC(O)R^7$;

or $R^5$ and $R^6$ together with the nitrogen atom to which they are bonded can combine to form a 5 to 12-membered heterocyclo ring optionally substituted with $T^{1g}$, $T^{2g}$ and $T^{3g}$;

$R^7$ is
  (1) hydrogen; or
  (2) alkyl, alkenyl, alkynyl, cycloalkyl, heterocyclo, aryl, heteroaryl, (cycloalkyl)alkyl, (heterocyclo)alkyl, (aryl)alkyl or (heteroaryl)alkyl each of which may be optionally independently substituted with $T^{1h}$, $T^{2h}$ and $T^{3h}$;

$T^{1a-1h}$, $T^{2a-2h}$, and $T^{3a-3h}$ are optional substituents independently selected from
  (1) V, where V is
    (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
    (ii) a group (i) which is itself substituted by one or more of the same or different groups (i); or
    (iii) a group (i) or (ii) which is independently substituted by one or more (preferably 1 to 3) of the following groups (2) to (13) of the definition of $T^1$;
  (2) —OH or —OV,
  (3) —SH or —SV,
  (4) —$C(O)_tH$, —$C(O)_tV$, or —O—$C(O)V$, where t is 1 or 2,
  (5) —$SO_3H$, —$S(O)_tV$, or $S(O)_tN(V^1)V$,
  (6) halo,
  (7) cyano,
  (8) nitro,
  (9) —$U^1$—$NV^2V^3$,
  (10) —$U^1$—$N(V^1)$—$U^2$—$NV^2V^3$,
  (11) —$U^1$—$N(V^4)$—$U^2$—V,
  (12) —$U^1$—$N(V^4)$—$U^2$—H,
  (13) oxo;

$U^1$ and $U^2$ are each independently
  (1) a single bond,
  (2) —$U^3$—$S(O)_t$—$U^4$—,
  (3) —$U^3$—C(O)—$U^4$—,
  (4) —$U^3$—C(S)—$U^4$—,
  (5) —$U^3$—O—$U^4$—,
  (6) —$U^3$—S—$U^4$—,
  (7) —$U^3$—O—C(O)—$U^4$—,
  (8) —$U^3$—C(O)—O—$U^4$—,
  (9) —$U^3$—C(=$NV^{1a}$)—$U^4$—, or
  (10) —$U^3$—C(O)—C(O)—$U^4$—;

$V^1$, $V^{1a}$, $V^2$, $V^3$ and $V^4$
  (1) are each independently hydrogen or a group provided in the definition of $T^1$; or
  (2) $V^2$ and $V^3$ may together be alkylene or alkenylene, completing a 3- to 8-membered saturated or unsaturated ring together with the atoms to which they are attached, which ring is unsubstituted or substituted with one or more groups listed in the definition of $T^1$, or
  (3) $V^2$ or $V^3$, together with $V^1$, may be alkylene or alkenylene completing a 3-to 8-membered saturated or unsaturated ring together with the nitrogen atoms to which they are attached, which ring is unsubstituted or substituted with one or more groups listed in the definition of $T^1$, or
  (4) $V^2$ and $V^3$ together with the nitrogen atom to which they are attached may combine to form a group —N=$CV^5V^6$ where $V^5$ and $V^6$ are each independently H or a group provided in the definition of V; and $U^3$ and $U^4$ are each independently
  (1) a single bond,
  (2) alkylene,
  (3) alkenylene, or
  (4) alkynylene;

provided that
  (1) groups -$J^1$-$R^1$ and -$J^2$-$R^2$ are not both hydrogen; and
  (2) when $J^1$ is —$NR^4$—,
    (a) neither $R^1$ or $R^4$ are a cephalosporin group of formula

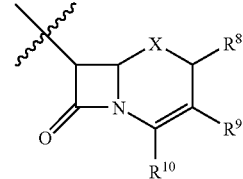

wherein
  X is O, S, $NR^{11}$, or $CH_2$;
  $R^8$ is hydrogen or alkyl
  $R^9$ is alkyl optionally substituted with —$OC(O)CH_3$ or —S-(tetrazolyl) wherein the tetrazole ring is optionally subtituted with alkyl;
  $R^{10}$ is COOH;
  $R^{11}$ is hydrogen, alkyl, formyl, or benzyl; and
  (b) $R^1$ and $R^4$ are not both hydrogen when -$J^2$-$R^2$ is hydrogen.

2. The compound according to claim 1, wherein:
  $J^1$ is a bond;
  $J^2$ is a bond;
  $J^3$ is alkylene or cycloalkylene either of which may be optionally substituted with $T^{1a}$, $T^{2a}$ and $T^{3a}$;
  M is hydrogen;
  $R^1$ is alkyl, aryl or heteroaryl any of which may be optionally substituted with $T^{1c}$, $T^{2c}$ and $T^{3c}$;
  $R^2$ is aryl or heteroaryl either of which may be optionally substituted with $T^{1d}$, $T^{2d}$ and $T^{3d}$;
  $R^3$ is —$NR^{3a}SO_2Z$;
  $R^{3a}$ is H or alkyl;
  Z is —$NR^5R^6$, or aryl optionally substituted with $T^{1f}$, $T^{2f}$ and $T^{3f}$;

R⁵ is
  (1) hydrogen; or
  (2) alkyl or (aryl)alkyl either of which may be optionally substituted with $T^{1g}$, $T^{2g}$ and $T^{3g}$;

R⁶ is
  (1) hydrogen; or
  (2) alkyl, aryl, heteroaryl, heterocyclo, (aryl)alkyl, (heteroaryl)alkyl, or (heterocylo)alkyl, any of which may be optionally substituted with $T^{1g}$, $T^{2g}$ and $T^{3g}$;
  (3) —C(O)OR⁷;

or R⁵ and R⁶ together with the nitrogen atom to which they are bonded combine to form a 5 to 10-membered heterocyclo ring (such as piperazine, piperadine, morpholine, pyrolidine, pyrazoldine, oxazolidine, 1,4-dioxa-8-aza-spiro[4.5]decane, or 1,3,8-Triaza-spiro [4.5]decane) which may be optionally substituted with $T^{1g}$, $T^{2g}$ and $T^{3g}$; and R⁷ is alkyl, aryl, (aryl)alkyl, any of which may be optionally substituted with $T^{1h}$, $T^{2h}$ and $T^{3h}$.

3. The compound according to claim 2, wherein:
J¹ is a bond;
J² is a bond;
J³ is alkylene or cycloalkylene;
M is hydrogen;
R¹ is phenyl thiazole, pryidine, thiophene, any of which may be optionally substituted with $T^{1c}$, $T^{2c}$ and $T^{3c}$ especially where $T^{1c}$, $T^{2c}$ and $T^{3c}$ are independently selected from alkyl, —OV halo, and nitro;
R² phenyl benzofuran, or pyridine any of which may be optionally substituted with $T^{1d}$, $T^{2d}$ and $T^{3d}$ wherein $T^{1d}$, $T^{2d}$ and $T^{3d}$ are independently selected from alkyl, haloalkyl, halo, —OV and —S(O)ₜV;
R³ is —NR³ᵃSO₂Z;
R³ᵃ is H;
Z is —NR⁵R⁶, or phenyl optionally substituted with $T^{1d}$, $T^{2d}$ and $T^{3d}$ wherein $T^{1d}$, $T^{2d}$ and $T^{3d}$ are independently selected from alkyl, halo, —C(O)ₜH, —C(O)ₜV, or —U¹—N(V⁴)—U²—V;
R⁵ is hydrogen, or alkyl optionally substituted with $T^{1g}$ wherein $T^{1g}$ is —U¹—NV²V³ wherein U¹ is a bond, and V² and V³ are independently hydrogen, alkyl, aryl or (aryl)alkyl);
R⁶ is
  (1) alkyl optionally substituted with $T^{1g}$, $T^{2g}$ and $T^{3g}$, wherein $T^{1g}$, $T^{2g}$ and $T^{3g}$ are independently selected from —U¹—NV²V³ where U¹ is a bond, and V² and V³ are independently hydrogen, alkyl, aryl or (aryl)alkyl wherein said aryl groups are optionally substituted with alkyl),
  (2) aryl, heteroaryl, (aryl)alkyl, or (heteroaryl)alkyl, any of which may be optionally substituted with $T^{1g}$, $T^{2g}$ and $T^{3g}$ wherein $T^{1g}$, $T^{2g}$ and $T^{3g}$ are independently selected from alkyl, —OV, haloalkyl, halo, —U¹—NV²V³ wherein U¹ is a bond, and V² and V³ are independently hydrogen, alkyl, aryl or (aryl)alkyl wherein said aryl groups are optionally substituted with alkyl), heterocyclo, or (aryl)alkenyl where the aryl group is optionally substituted with —U¹—NV²V³;
  (3) heterocyclo or (heterocylo)alkyl, either of which may be optionally substituted with $T^{1g}$, $T^{2g}$ and $T^{3g}$ wherein $T^{1g}$, $T^{2g}$ and $T^{3g}$ are independently selected from, alkyl, —C(O)ₜH, —C(O)ₜV whereis V is alkyl), (aryl)alkyl wherein the aryl group is optionally substituted with one or more haologen, haloalkyl, or alkynyl); or
  (4) —C(O)OR⁷;

or R⁵ and R⁶ together with the nitrogen atom to which they are bonded combine to form piperazine, piperadine, morpholine, pyrolidine, pyrazoldine, oxazolidine, 1,4-dioxa-8-aza -spiro[4.5]decane, or 1,3,8-Triaza-spiro [4.5]decane any of which may be optionally substituted with $T^{1g}$, $T^{2g}$ and $T^{3g}$ wherein $T^{1g}$, $T^{2g}$ and $T^{3g}$ are independently selected from alkyl (optionally substituted with alkoxy, or hydroxy), (heterocyclo)alkyl, aryl (optionally substituted with one or more alkoxy, halo, alkyl, haloalkyl, or nitro), (aryl)alkyl (wherein the aryl group is optionally further substituted with one or more alkoxy, halo, alkyl, haloalkyl, or nitro), —C(O)ₜH, —C(O)ₜV (especially where V is alkyl), alkenyl, (aryl)alkenyl, cycloalkyl, heteroaryl (optionally substituted with cyano, alkyl, or haloalkyl), oxo, hydroxy, alkoxy, heterocyclo, or nitro; and R⁷ is alkyl, aryl, or (aryl)alkyl, wherein said aryl groups are optionally further substituted with one or more alkyl groups.

4. A pharmaceutical composition, comprising a compound according to claim 1 and a pharmaceutically acceptable carrier therefor.

* * * * *

UNITED STATES PATENT AND TRADEMARK OFFICE
CERTIFICATE OF CORRECTION

PATENT NO. : 7,432,271 B2  Page 1 of 2
APPLICATION NO. : 10/932981
DATED : October 7, 2008
INVENTOR(S) : Khehyong Ngu et al.

It is certified that error appears in the above-identified patent and that said Letters Patent is hereby corrected as shown below:

Cover Page, Col. 2, (Other Publications), line 7, delete "macrophase" and insert -- macrophage --;

Claim 1, col. 82, line 38, delete "$T^{3a}$." and insert -- $T^{3a}$; --;

Claim 1, col. 84, line 48, delete "subtituted" and insert -- substituted --;

Claim 2, col. 85, line 14, delete "pyrazoldine" and insert -- pyrazolidine --;

Claim 3, col. 85, line 25, delete "phenyl thiazole, pryidine, thiophene" and insert -- phenyl, thiazole, pyridine, pyrimidine, or thiophene --;

Claim 3, col. 85, line 27, delete "where" and insert -- wherein --;

Claim 3, col. 85, line 28, delete "OV halo" and insert -- OV, halo --;

Claim 3, col. 85, line 29, delete "phenyl benzofuran, or pyridine any" and insert -- is phenyl, benzofuran, or pyridine, any --;

Claim 3, col. 85, line 42, delete "(aryl)alkyl);" and insert -- (aryl)alkyl; --;

Claim 3, col. 85, line 44, delete "$T^{3g}$," and insert -- $T^{3g}$ --;

Claim 3, col. 86, line 1, delete "where" and insert -- wherein --;

Claim 3, col. 86, line 4, delete "alkyl)," and insert -- alkyl, --;

Claim 3, col. 86, line 11, delete "alkyl)," and insert -- alkyl, --;

Claim 3, col. 86, lines 17-18, delete "whereis V is alkyl), (aryl)alkyl" and insert -- wherein V is alkyl, or (aryl)alkyl --;

Signed and Sealed this

Eighteenth Day of May, 2010

David J. Kappos
*Director of the United States Patent and Trademark Office*

CERTIFICATE OF CORRECTION (continued)
U.S. Pat. No. 7,432,271 B2

Claim 3, col. 86, line 19, delete "haologen," and insert -- halogen, --;

Claim 3, col. 86, line 20, delete "nyl)" and insert -- nyl --;

Claim 3, col. 86, line 24, delete "pyrazoldine" and insert -- pyrazolidine --; and Claim 3, col. 86, line 34, delete "(especially where V is alkyl)," and insert -- wherein V is alkyl," --.

UNITED STATES PATENT AND TRADEMARK OFFICE
CERTIFICATE OF CORRECTION

PATENT NO. : 7,432,271 B2
APPLICATION NO. : 10/932981
DATED : October 7, 2008
INVENTOR(S) : Ngu et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 523 days Delete the phrase "by 523 days" and insert -- by 846 days --

Signed and Sealed this

Seventh Day of September, 2010

David J. Kappos
*Director of the United States Patent and Trademark Office*